United States Patent
Nunan et al.

(10) Patent No.: US 10,716,578 B2
(45) Date of Patent: Jul. 21, 2020

(54) SURGICAL BLADE CARTRIDGE WITH A GUIDE BAR HAVING FEATURES TO CONTROL THE DEPTH OF THE CUT FORMED WITH THE CARTRIDGE

(71) Applicant: Stryker European Holdings I, LLC, Kalamazoo, MI (US)

(72) Inventors: Gerard Nunan, Ballincolig (IE); James Walen, Portage, MI (US); David Goldenberg, Mattawan, MI (US)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 0 days.

(21) Appl. No.: 16/081,449

(22) PCT Filed: Mar. 3, 2017

(86) PCT No.: PCT/US2017/020731
§ 371 (c)(1),
(2) Date: Aug. 31, 2018

(87) PCT Pub. No.: WO2017/155821
PCT Pub. Date: Sep. 14, 2017

(65) Prior Publication Data
US 2019/0192170 A1 Jun. 27, 2019

Related U.S. Application Data

(60) Provisional application No. 62/304,160, filed on Mar. 5, 2016.

(51) Int. Cl.
A61B 17/14 (2006.01)
B27B 19/00 (2006.01)
B23D 49/10 (2006.01)
A61B 17/15 (2006.01)

(52) U.S. Cl.
CPC .......... *A61B 17/142* (2016.11); *A61B 17/144* (2016.11); *B23D 49/10* (2013.01);
(Continued)

(58) Field of Classification Search
CPC ..... A61B 17/14; A61B 17/142; A61B 17/144; A61B 17/147; A61B 17/15;
(Continued)

(56) References Cited

U.S. PATENT DOCUMENTS 5,363,711 A * 11/1994 Seto ...................... B27B 19/006
30/500
6,001,115 A * 12/1999 Ahola .................. A61B 17/144
606/176

(Continued)

FOREIGN PATENT DOCUMENTS

DE 3640516 C1 4/1998
DE 202007010079 U1 11/2007

OTHER PUBLICATIONS

International Search Report for PCT/US2016/066633 dated Jul. 12, 2017.
(Continued)

*Primary Examiner* — Larry E Waggle, Jr.
(74) *Attorney, Agent, or Firm* — Howard & Howard Attorneys PLLC

(57) ABSTRACT

A blade cartridge for use with a surgical saw includes a bar and a rack. The bar includes a first holding feature for removably holding the bar static to the saw. The rack includes a base moveably disposed in the bar and has cutting teeth defining extending beyond the bar. A drive link extends from the base, providing a second holding feature for releasably engaging a reciprocating drive integral with the saw. One of the base and the bar includes a guide slot. The other of the base and the bar includes a static member
(Continued)

extending into the guide slot. The guide slot and the static member allow the rack to reciprocally move from proximal to distal to proximal along a longitudinal axis of the bar. The bar includes two plates and a spacer between the plates. The base is located between the plates.

20 Claims, 21 Drawing Sheets

(52) U.S. Cl.
CPC .............. *B27B 19/00* (2013.01); *A61B 17/15* (2013.01); *B27B 19/006* (2013.01)

(58) Field of Classification Search
CPC .... B23D 49/10–16; B23D 51/10; B26B 7/00; B26B 7/005; B27B 19/00–008; B27B 19/09
See application file for complete search history.

(56) References Cited

U.S. PATENT DOCUMENTS

| | | | |
|---|---|---|---|
| 6,302,406 B1* | 10/2001 | Ventura | B23D 49/16 279/48 |
| 7,497,860 B2* | 3/2009 | Carusillo | A61B 17/157 606/82 |
| 7,704,254 B2 | 4/2010 | Walen | |
| 8,323,285 B2* | 12/2012 | Walen | A61B 17/142 29/428 |
| 2006/0009796 A1 | 1/2006 | Carusillo et al. | |
| 2007/0119055 A1 | 5/2007 | Walen et al. | |
| 2008/0243125 A1 | 10/2008 | Guzman et al. | |
| 2014/0163558 A1* | 6/2014 | Cosgrove | A61B 17/142 606/82 |
| 2018/0064448 A1* | 3/2018 | Mac an Tuile | B23D 51/16 |

OTHER PUBLICATIONS

English language abstract and machine-assisted English translation for DE 3640516 extracted from espacenet.com database on Sep. 7, 2018, 15 pages.

English language abstract and machine-assisted English translation for DE 202007010079 extracted from espacenet.com database on Sep. 7, 2018, 30 pages.

* cited by examiner

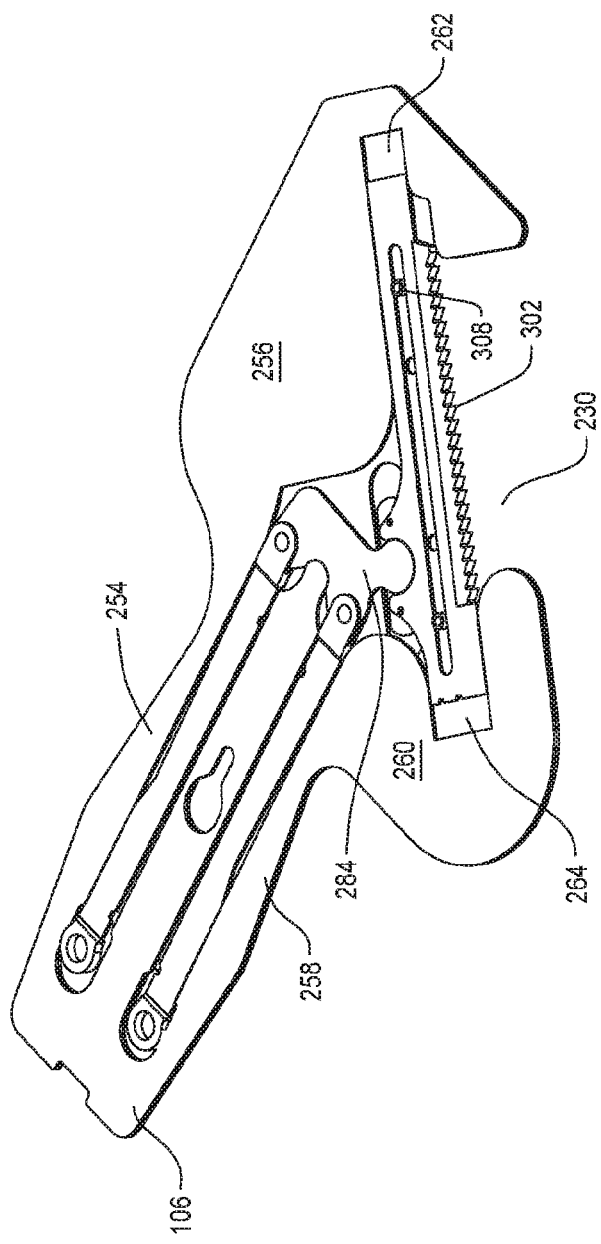
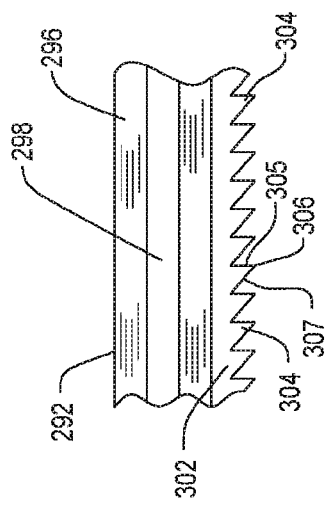
FIG. 11
FIG. 11A

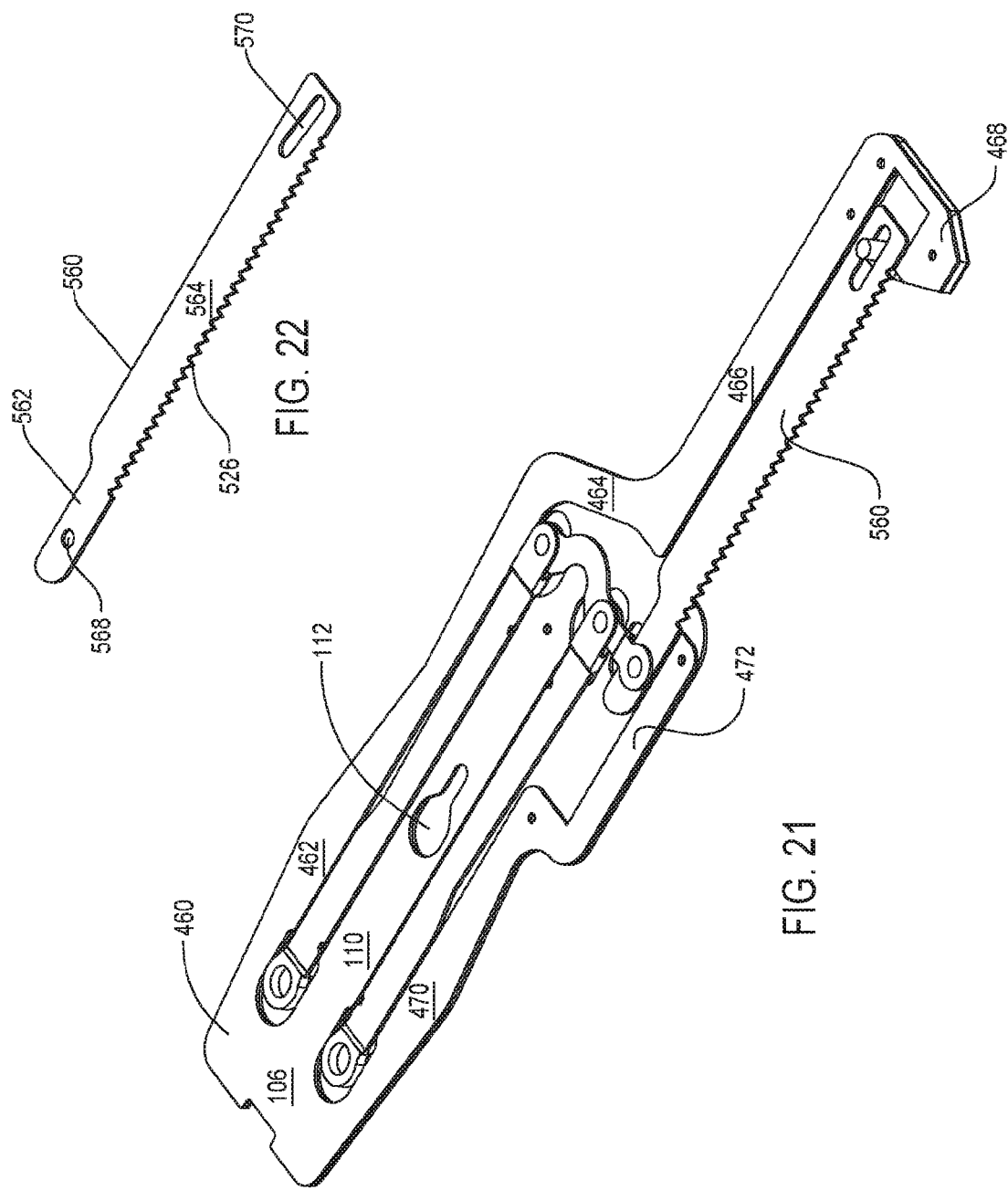

SURGICAL BLADE CARTRIDGE WITH A GUIDE BAR HAVING FEATURES TO CONTROL THE DEPTH OF THE CUT FORMED WITH THE CARTRIDGE

FIELD OF THE INVENTION

This invention relates to a surgical blade cartridge that has a static guide bar and a blade that is pivotally mounted to the bar. More particularly, this invention is related to a surgical blade cartridge with a static guide bar that includes structural members useful for controlling the depth of the cut formed by the cartridge.

BACKGROUND OF THE INVENTION

A surgical saw blade is used to cut the tissue against which the blade is applied. Many surgical saw blades are configured to cut hard tissue, bone. A sagittal surgical saw blade is a surgical saw blade with a head that pivots around an axis that is perpendicular to the plane of the blade. Some surgical saw blades are known as reciprocating saw blades. This type of blade is designed to so the body of the blade moves back and forth along the longitudinal axis that extends along, though, the body of the blade. Both types of saw blade include features that facilitate the releasable attachment of the blade to the saw used to actuate the blade. The saw includes a motor. When the saw motor is actuated, the saw moves the blade in a back and forth pattern. As implied by the name, a reciprocating blade is, when actuated, considered to reciprocate back and forth. A sagittal saw blade, when actuated, is often considered to oscillate back and forth around a pivot point.

PCT Pub. No. WO 2006/017066A2/U.S. Pat. No. 7,497,860 and PCT Pub. No. WO 2007/030793/U.S. Pat. No. 7,704,254, the contents of both of which are incorporated herein by reference, each disclose a sagittal saw blade cartridge. A sagittal saw blade cartridge includes a static guide bar and a blade. The guide bar is an elongated assembly that is releasably attached to the handpiece, the saw, that actuates the cartridge. The blade is pivotally mounted to the guide bar. The blade has teeth that extend forward of the guide bar. Also part of the cartridge and internal to the guide bar are one or more drive links. Each drive link extends from the blade towards the proximal end of the guide bar. The drive links are reciprocated back and forth by a drive assembly internal to the saw. The reciprocation of the drive links causes the blade to pivot, to oscillate, back and forth. The pivoting of the blade is what enables the teeth to cut the tissue against which the blade is pressed. Sometimes, this type of cartridge is referred to as an oscillating tip saw blade cartridge.

An advantage of the sagittal surgical blade cartridge is that the only portion of the cartridge that pivots is the distally located blade. In contrast, a conventional sagittal saw blade pivots from its point of attachment to the saw to which the blade is attached. As a consequence the saw to which a cartridge is attached vibrates less than the saw to which a conventional sagittal saw blade is attached. Thus, the saw to which a sagittal surgical blade cartridge is attached can be easier to control than a saw to which a conventional surgical sagittal saw blade is attached. Also, it is common practice to use a cutting guide to properly position a sagittal saw blade relative to the tissue the blade is intended to cut. When a conventional blade is actuated, the oscillating movement of the blade wears against the surfaces of the cutting guide defining the slot in which the blade is seated. The guide bar of a surgical sagittal blade cartridge only minimally moves in this slot. Thus, by using a cartridge, instead of a conventional blade, less of the material forming the cutting guide is rubbed off the guide. This reduces the extent to which the surgeon has to flush worn off cutting guide material from the surgical site. Further, use of the oscillating tip blade reduces the extent to which the material forming the guide becomes so worn that the guide itself is rendered useless.

A surgical sagittal blade cartridge has another benefit over a conventional sagittal saw blade. Since the guide bar remains static when the blade is actuated, the practitioner can press one or more fingers against the guide bar. This facilitates the holding of the cartridge in the desired position as the cartridge is advanced against the tissue that is to be cut.

PCT Pub. No. WO 2006/017066A2/U.S. Pat. No. 7,497,860 also discloses a reciprocating blade cartridge. This cartridge has a blade that extends laterally, from a side of the bar portion of the cartridge. A drive rod internal to the bar reciprocates the blade back and forth along an axis that is parallel to the proximal-to-distal longitudinal axis through the bar. The Applicant's U.S. Prov. Pat. App. No. 62/268,536, the contents of which are explicitly incorporated by reference and contained in U.S. patent application Ser. No. 16/062,727/PCT Pub. No. WO 2017/106533 A2 also discloses a reciprocating blade cartridge.

Surgical blade cartridges work well for the purposes for which they are designed. Nevertheless, a surgical blade cartridge shares a limitation with a conventional surgical saw blade. It can be difficult for the surgeon pressing the blade cartridge against bone to control the depth of the cut of the cut of formed by the cartridge. Essentially a surgeon has to rely on the feel of the saw and cartridge to determine if the blade has formed the desired cut and the surgeon should stop applying a forward force to the cartridge. It is desirable to so stop plunging the blade forward because it is typically undesirable to allow the cartridge to cut the soft tissue inwardly of the bone. To ensure that blade cartridge does not advance beyond the desired depth, the surgeon is required to control the force applied to the saw. Specifically the force needs to be sufficient to overcome the resistive force of the bone against which the blade is applied. The force, however, cannot be so great that, when the blade breaks through the bone, the momentum of the saw, results in the appreciable advancement of the blade through the underlying soft tissue. Simultaneously with having to so regulate the force applied to the saw and cartridge, the surgeon needs to tactilely sense the change in the resistive force to which the cartridge is exposed. The sensing of the sudden drop off of this force functions as the cue that the cartridge has cut through the bone being cut and that it is necessary to stop applying a forward force to the saw and the blade.

Having to simultaneously perform these control and sensing steps can add to the physical and mental stress associated with applying either a sagittal saw blade or a sagittal saw blade cartridge to the bone in which the cut is to be formed.

Further, there are a number procedures for which the most appropriate blade to form the cut bone is the reciprocating blade. This is true for procedures that involve forming cuts in the jaw. This is also true in many situations when it is necessary to form a cut in the sternum, the bone that covers the heart and lungs. When performing this type of procedure, the motion and shape of the sagittal blade typically does not make it possible to use this type of blade to form the desired cut. The incorporated by reference PCT Pub. No. WO 2006/017066A2/U.S. Pat. No. 7,497,860 discloses a sagittal saw blade cartridge with a blade that projects laterally, from the side of the guide bar. Even this type of sagittal blade cartridge has not proven to be a suitable replacement for a reciprocating saw blade. There are some reciprocating saws specifically designed to use a reciprocating blade especially designed to cut through the sternum. This means that a facility that performs both orthopedic surgery and surgery on the chest must have two types of saws available. A first saw needs to be provided to drive the sagittal blades used by an orthopedic surgeon. A second saw needs to be provided to drive the reciprocating blade a chest surgeon uses to access organs and tissue below the sternum.

SUMMARY OF THE INVENTION

This invention relates to a new and useful surgical blade cartridge. The blade cartridge of this invention includes a bar and a blade that is mounted to the bar for oscillatory motion. Here oscillatory motion is understood to be repetitive back and forth motion. The surgical blade cartridge of this invention includes features that are useful for regulating the positon of the cartridge relative to the bone against which the cartridge is applied. These features are associated with the guide bar of the cartridge.

It is still a further feature of this invention to provide a reciprocating blade cartridge that can be used like a conventional reciprocating blade and is further constructed so the locus of movement of the blade is spaced from the saw used to actuate the blade. A further feature of this cartridge is that it can be attached to a saw designed to actuate the blade of a sagittal blade cartridge.

In many versions of the invention, the feature of the cartridge of this invention useful for limiting plunge is a structural member of the static guide bar that is located adjacent the space in which the teeth of the blade move back and forth. Typically this structural member is located adjacent one end of the space in which the teeth move. In some embodiments of this invention this structural member extends at least partially forward of the proximal end of the space in which the teeth move. In still other versions of the invention, this structural member extends forward of the space in which the teeth move. In some versions of the invention, the cartridge has plural extensions. Separate extensions are located on opposed sides the blade.

In some versions of this invention, this extension is an arm. The arm is constructed so the distal end of the arm is located laterally away from the teeth of the blade. When the cartridge is pressed against bone, the distal end of the arm rests against an uncut section of the bone. The uncut section of bone thus becomes a fulcrum point around which the arm pivots as the blade is rotated into tissue.

In some embodiments of this version of this version of the invention the bar is formed with two arms. Also in some versions of this invention, the arm is located so, longitudinally along the cartridge, the arm is located distal to the proximalmost sweep position of the blade and proximal to the distal end of the blade.

In still other versions of the invention, the structural member of the guide bar includes a surface located forward of the blade. In these versions of the invention, the surface functions as a stop that limits the proximal movement of the cartridge away from the bone against which the cartridge is applied. The surface allows the blade to be used as a sternum saw.

In some embodiments of this version of the invention the blade is formed so the teeth are arranged linearly. Often in these embodiments of the invention, the cartridge is further formed so the blade reciprocates back and forth along an axis that intersects the longitudinal axis of the cartridge. In some of these embodiments of the invention, the blade is mounted to the cartridge so the head moves along a line that is not perpendicular to the longitudinal axis of the blade cartridge. It should also be understood that a cartridge of this invention may be configured so that cartridge blade undergoes a loop motion. This motion includes a longitudinal component in which a point on the blade engages in at least some repetitive proximal-to-distal motion. The same motion has a lateral component. The point engages in some repetitive side-to-side motion. Since the blade engages in some longitudinal motion the blade for the purposes of this invention is considered to engage in reciprocal motion.

Embodiments of both versions of this invention are often constructed so the blade projects outwardly beyond the sides of the proximal end of the guide bar. In these embodiments of the invention the cartridge is thus further formed so the guide bar can be said to have a proximally located foot and a distally located head. The foot is the portion of the bar mounted to the saw used to actuate the cartridge. The head, which is located forward of the foot, is the portion of the cartridge from which the blade and one or more arms extend. Owing to the relatively large width of the blade, in comparison to the bar foot, the bar head is also typically larger in side-to-side width than the bar foot.

Some blade cartridges of this invention are designed so the blade oscillates around an axis that extends through the plane of the blade. These versions of the invention are sometimes referred to as a surgical sagittal blade cartridges.

Other blade cartridges of this invention include a blade that oscillates back and forth along a line that is coplanar if not parallel to the longitudinal axis through the static guide bar. These versions of the invention are sometimes referred to as surgical reciprocating blade cartridges. These versions of the invention include the drive links and blades of the basic cartridge of this invention. These versions of the invention also include pivot link. The pivot link transfers to reciprocal motion of the drive links to the blade so as to cause the reciprocal movement of the blade.

BRIEF DESCRIPTION OF THE DRAWINGS

The invention is pointed out with particularity in the claims. The above and further features and benefits of the invention are understood from the following Detailed Description taken in conjunction with the accompanying drawings in which:

FIG. 11 is a perspective view of the cartridge of FIG. 7 with the top plate removed;

FIG. 11A is a an enlarged plan view of a section of the blade of the cartridge of FIG. 7;

FIG. 21 is a perspective view of the cartridge of FIG. 17 with the top plate removed and an alternative blade seated in the guide bar; and FIG. 22 is a perspective view of the blade of FIG. 21.

DETAILED DESCRIPTION

I. First Cartridge

Figure 1:
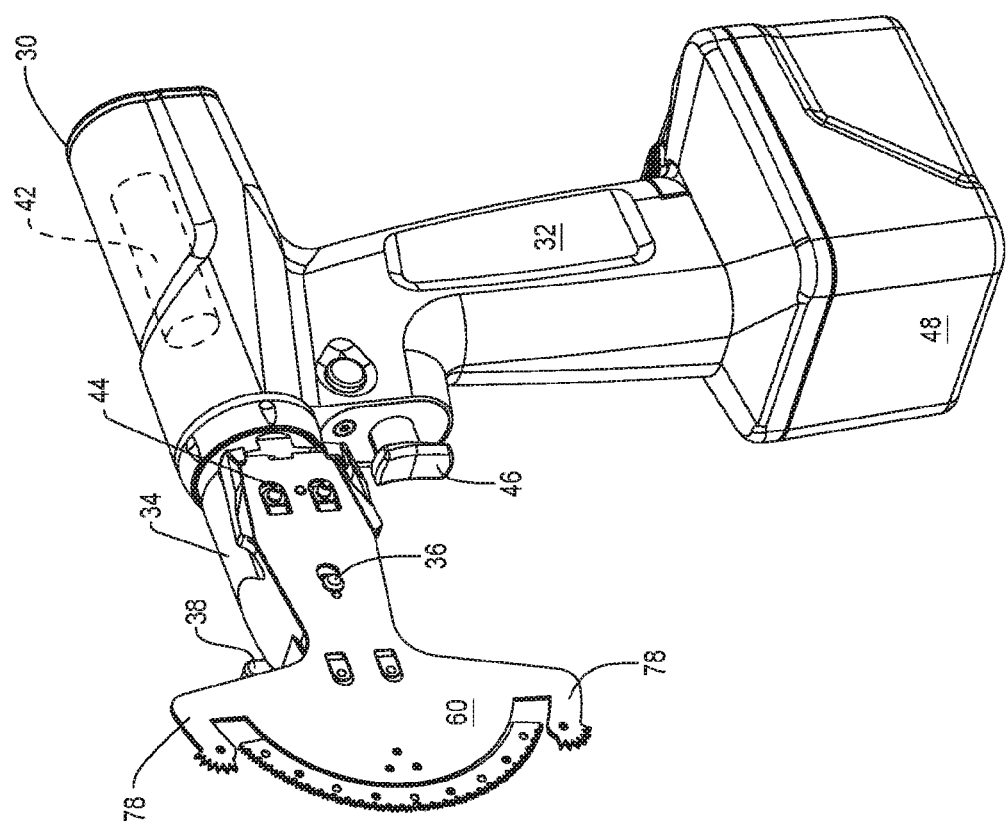
FIG. 1 is a perspective view of a first surgical blade cartridge of this invention attached to a saw used to actuate the cartridge.

FIG. 1 illustrates a saw 30 to which a surgical sagittal blade cartridge 60 of this invention is removably attached. Saw 30 includes a body or housing 32. In the depicted version of the invention, housing 32 is pistol shaped. A head 34 extends distally forward from the distal end of the housing 32 and is the most distal component of the saw 30, (Here, "distal" is understood to means away from the surgeon holding the saw 30; towards the site to which the cartridge 60 is applied. "Proximal" is understood to mean towards the surgeon holding the saw 30; away from the site to which the cartridge 60 is applied.) The head 34 is shaped to receive the proximal end of cartridge 60. A coupling rod 36, the head of which is seen, is slidably mounted to the saw head 34. When coupling rod 36 is in the run position, a portion of the rod presses against the cartridge 60 to hold the cartridge to the head 34. When the coupling rod 36 is in the load position, the coupling rod 36 does not press against cartridge 60. This allows the cartridge 60 to be removed from the head and a new cartridge releasably attached to the head. A wing nut 38, partially seen, attached to the head 34 moves the coupling rod 36 between the run and load positions.

A motor 42, represented by a phantom cylinder, is disposed inside the barrel of housing 32. Motor 42 is connected to a pair of drive pins 44, one pin identified, that are mounted to the head 34 to project above the surface on which the cartridge 60 is seated. Drive pins 44 are mounted to the head 34 to engage in opposed oscillatory motion. A trigger 46, located below the saw head 34, is the manually actuated member that is depressed to control the actuation of the saw. A battery 48 is seen attached to the butt end of the grip portion of the housing 32. In the depicted version of the invention, motor 42 is an electric motor. Battery 48 provides the current required to energize the motor 42.

Figure 2:
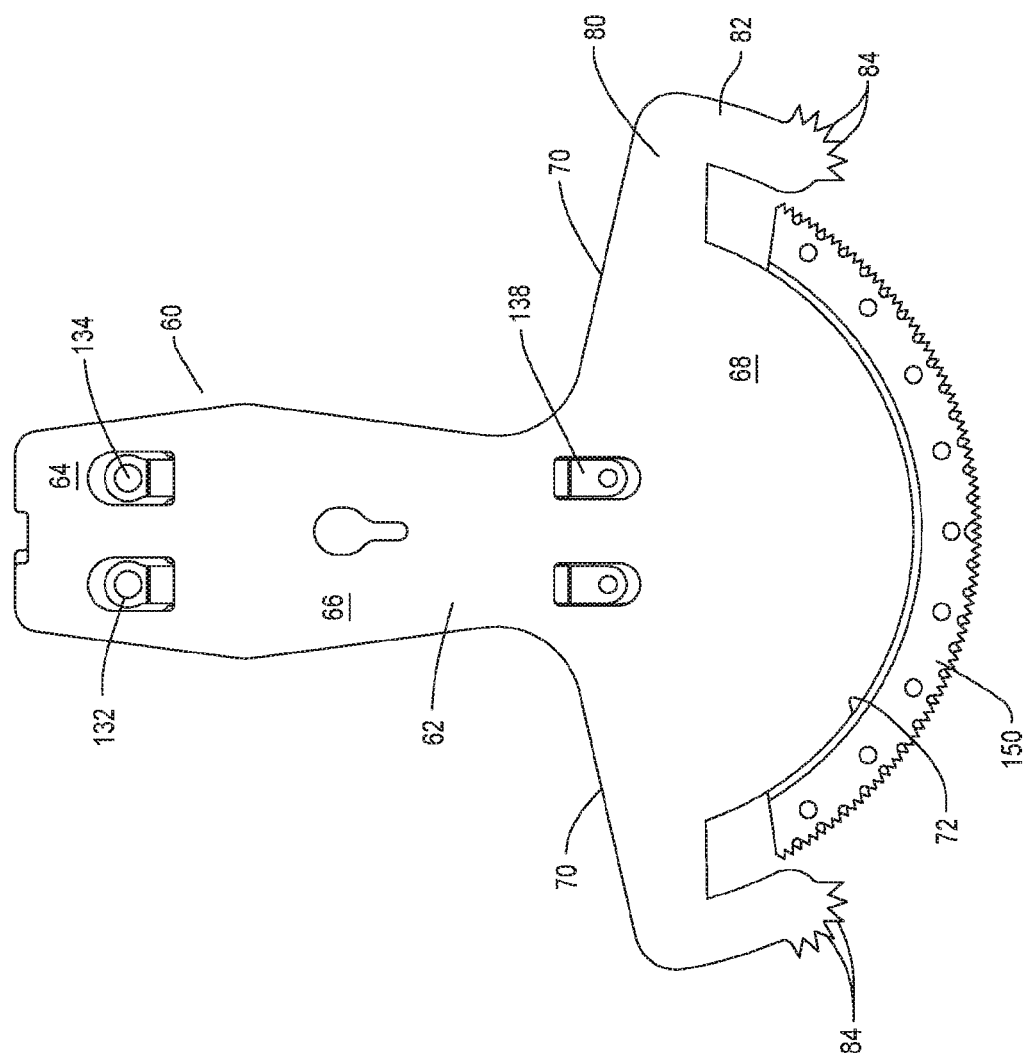
FIG. 2 is a plan view of the cartridge of FIG. 1.
Figure 3:
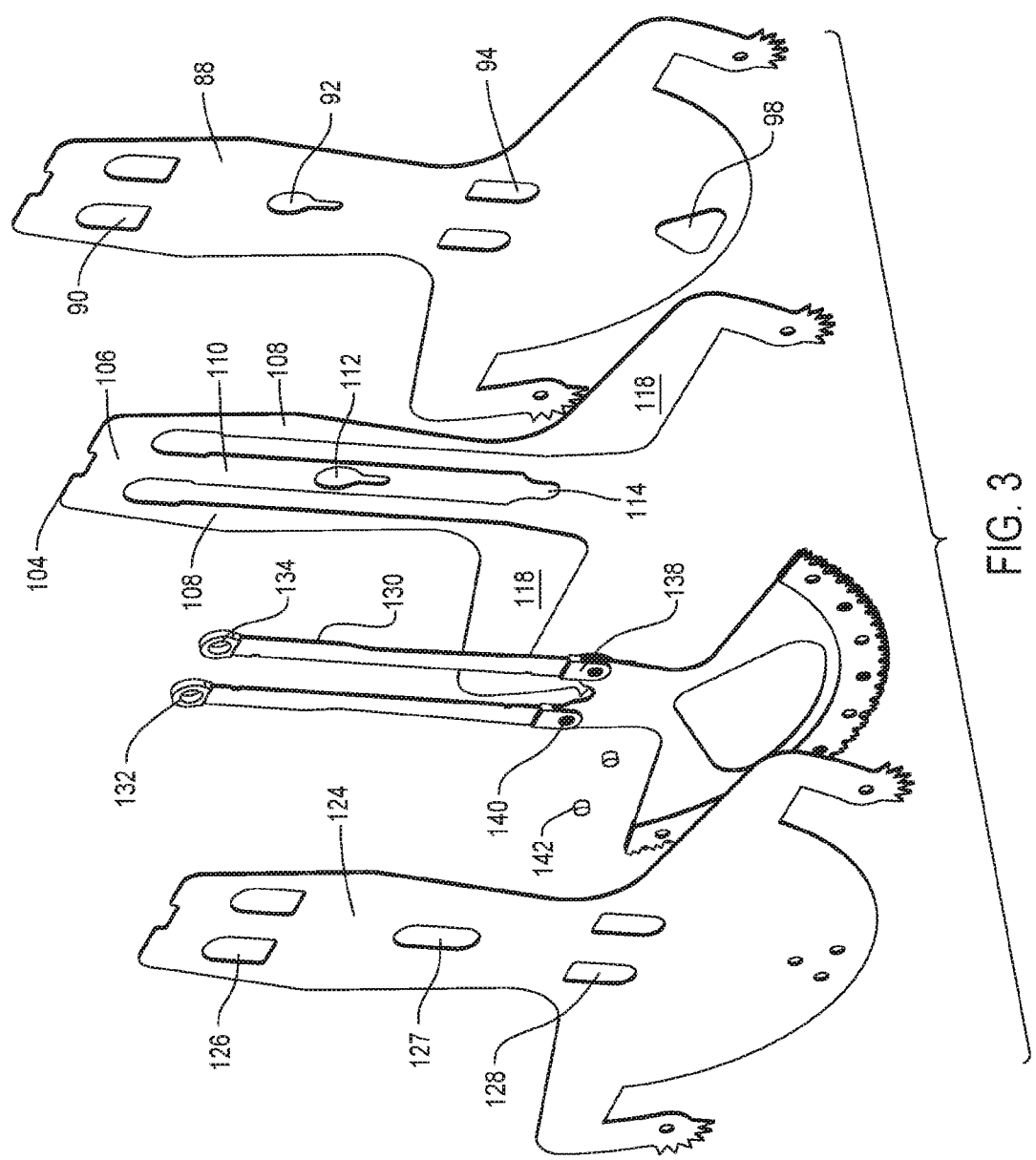
FIG. 3 is an exploded view of the cartridge of FIG. 1.

The cartridge 60, as seen in FIGS. 2 and 3, includes a guide bar 62 to which a blade 150 is pivotally mounted. Drive links 130, one link identified, extend proximally from opposed sides of the blade 150. The drive links 130 terminate at a location forward of the proximal end of the guide bar 62.

Guide bar 62 is a laminate structure that includes a bottom plate 88 and an inner plate 104 disposed over the bottom plate 88. A top plate 124, also part of the guide bar 62, is secured over the exposed face of the inner plate 88. Collectively, plates, 88, 104 and 124 are formed so the guide bar 62, at the proximal end, has a foot 64. Foot 64 is shaped so that, extending from the proximal end of the foot, which is the proximal end of the guide bar 62, the sides of the foot taper slightly outwardly. Forward of the foot 64, plates 88, 104 and 124 are shaped so the guide bar has a trunk 66. From where the trunk 66 extends forward from the foot 64, the sides of the guide bar 62 taper inwardly.

At the distal end of the trunk 66, guide bar 62 is shaped to have a head 68. Head 68 is the most distal portion of the guide bar. The guide bar head 68 is shaped to have two opposed outwardly extending back faces 70, the edges of which are identified in FIG. 2. Each face 70 extends laterally outwardly from the distal end of the adjacent side of the trunk 66. In the illustrated version of the invention, the guide bar 62 is formed so that as each face 70 extends laterally outwardly, the face extends a short distance distally forward. The bottom plate 88 and top plate 124 are formed to, forward of the back faces 70 provide the guide bar with a distally directed, curved front face 72, the edge of which is identified in FIG. 2. Guide bar 62 is shaped so that the front face 72 subtends an angle between 110 and 180°. As discussed below, the guide bar is formed so that the inner plate 104 does not extend the same length as the bottom plate 88 and top plate 124. Accordingly, there is elongated slot 74 in the bar front face 72 between the inner and bottom and top plates 88 and 124, respectively. Slot 74 is identified in FIG. 5.

The guide bar 62 is further formed so that between each end of the back face 70 and the adjacent end of front face 72 an arm 78 (arms identified in FIG. 1) projects laterally outwardly from the head 68. Each arm 78 includes a base 80, one base identified in FIG. 2. The base 80 is the portion of the arm that projects laterally away from the head 68. A forearm 82, also part of the arm 78, one forearm identified in FIG. 2, extends longitudinally forward from the free end of the base. The free end of each forearm 82 is rounded. Fingers 84 protrude outwardly from the outer side surface of each forearm 82. Each finger 84 is triangular shape so as to have a pointed tip, (finger tips not identified). Owing to the free end of each forearm 82 being rounded, the fingers 84, appear to be arranged in a circular pattern around the forearm from which they extend.

Immediately forward of the proximal end of the plate, bottom plate 88 is formed to have two laterally spaced apart openings 90 (one identified). Top plate 124 is formed to have two openings 126 (one identified) that are each positioned to be in registration with a separate one of the bottom plate openings 90. Openings 90 and 126 are identical in shape. The bottom plate 88 is further formed to define two openings 94 (one opening identified). Openings 94 are located in the portion of the plate 88 that forms the proximal portion of the head portion of the plate. Each opening 94 is longitudinally aligned with a separate one of the openings 90. Top plate 124 is formed to have two openings 128. Each opening 128 is positioned to be in registration with a separate one of the bone plate openings 94. Openings 94 and 128 are identical in shape.

Bottom plate 88 is further formed to have a keyhole shaped opening 92. Opening 92 is longitudinally centered over the longitudinal axis of the plate 88. Opening 92 is located in the portion of the plate 88 that forms the proximal portion of the trunk section of the plate. The inner plate 104 is formed to have an identically shaped opening 112. The top plate 124 has an opening 127. When the plates 88, 104 and 124 are assembled together, bottom plate opening 92 and inner plate opening 112 are in registration. Top plate opening 127 is disposed over openings 92 and 112. Openings 92, 112 and 127 are collectively dimensioned to receive the head of saw coupling rod 36. A more complete understanding of this arrangement is disclosed in the now explicitly incorporated by reference U.S. Prov. Pat. No. 62/160,234 the contents of which are contained in PCT Pub. No. WO 2016/182981A2/ US Pat. Pub. No. 2018/0064448A1.

A triangular plate 98 is welded or otherwise secured to the inner face of the bottom plate 88. Plate 98 is located over the portion of the bottom plate 88 that forms a portion of the head 68 of the guide bar 62.

At the proximal end, inner plate 104 is formed to have a base 106. Two spaced apart outer tines 108 extend distally forward from the opposed ends of base 106. An inner tine 110 extends forward from the center of the base 106. The inner plate 104 is formed so that the outer tines 108 are laterally spaced away from the inner tine 110. The inner tine 110 is the portion of the inner plate in which opening 112 is formed. It is further observed that the inner tine 110 is formed to have a distal end head 114 that is rounded in shape.

The inner plate 104 is further formed so a beam 118 extends laterally outwardly from the distal end of each outer tine 108. Beams 118 are portions of the inner plate 104 that are the structural components of the plate 104 that form part of the guide bar head 68. The L-shaped outer end of each inner beam 118 is the section of the beam that is the structural component of the inner plate 104 that form part of the arm 78 and fingers 84 on the side of the bar with which the beam is associated.

Top plate 124 is essentially identical in shape to the bottom plate 88. One difference between the two plates 88 and 124 is that there is no supplemental plate welded or otherwise secured to the inner surface of the top plate 124.

Figure 4:
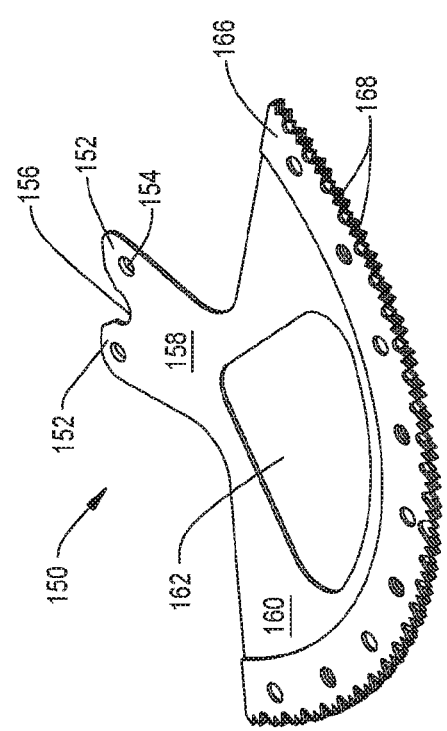
FIG. 4 is a perspective view of the blade internal to the cartridge of FIG. 1.

The blade 150, as seen in FIG. 4, is formed to have a proximal web 158. The blade 150 is formed so that web 158 has a thickness that is no greater than the thickness of inner plate 104. Web 158 is generally trapezoidal in shape. The proximal end of the web 158 is the widest portion of the web. When blade 150 is in the centered position within the guide bar 62 the major axis of the web 158 is collinear with the major axis of the guide bar. Extending proximally from web 158 and away from the longitudinal axis of the web, blade 150 is shaped to have two feet 152. Feet 152 have the same thickness of web 158. Each foot 152 extends between one of the outer tines 108 and the inner tine 110 of the adjacent inner plate 104. An opening 154, (one opening identified) extends top to bottom through each foot 152. Between the feet 152 blade 150 is formed to have a curved, proximally directed face 156, the edge of which is identified. The blade 150 is shaped so that blade face 156 can seat against and pivot around the head 114 integral with the inner tine 110.

A distal web 160 extends outwardly away from the distal end of the proximal web 158. Distal web 160 has the same thickness of the proximal web 158. Webs 158 and 160 can collectively considered the base of blade 150. Distal web 160 can thus oscillate in the space within the guide bar head 68 between the bottom and top plates 88 and 124, respectively. The distal web 160 extends laterally outwardly beyond the proximal web 158. The front face of distal web 160 is curved. More particularly, the components forming cartridge 60 are constructed so the curved distal face of the distal web will essentially be flush with the distal face of the head 68 of the guide bar. It should be understood that the arc subtended by distal web 160 is approximately 20 to 50° less than arc of the front face 72 of the cartridge bar head 68.

The blade 150 is further formed so as to have an opening 162 that extends side-to-side through the distal web 160.

Collectively, feet 152, proximal web 158 and distal web 160 are sometimes collectively referred to as the base of the blade 150.

An arcuately shaped head 166 extends outwardly around the outer distally directed edge of the distal web 160. Teeth 168 protrude outwardly from the head 166. Teeth 168 have a geometry that facilitate the cutting of the tissue, typically bone, the cartridge 60 is intended to cut. The geometry of the teeth 168 are not part of the present invention. The head 166 and, more particularly the teeth 168, have a side to side width that is greater than that of the base of the blade 160. Specifically, the width is large enough so the kerf the teeth form in the bone against which the cartridge 60 is applied is able to receive the guide bar 62. At a minimum, this typically means the teeth 168 have a width at least as great as the width between the opposed outer faces of the bottom and top plates 88 and 124, respectively.

Figure 5:
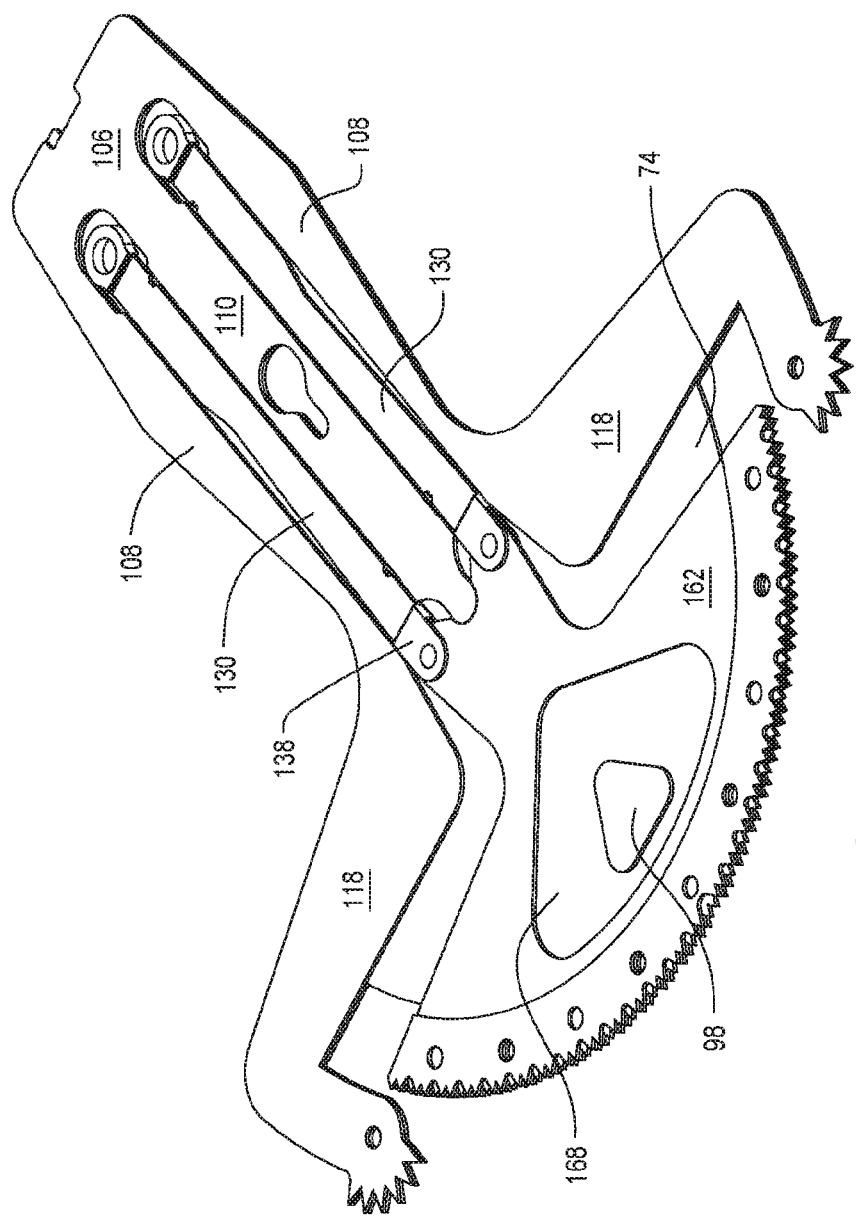
FIG. 5 is a perspective view of the cartridge of FIG. 1 with the top plate removed.

A drive link 130 is disposed in each of the elongated spaces on either side of the inner tine 110 of the inner plate 104 as seen in FIGS. 3 and 5. Each drive link 130 is in the form of an elongated flat strip of metal. The drive links 130 are formed so that, at the proximal end of each link, there is a foot 132, one foot identified. Each foot 132 is formed to have a center located through hole 134, one hole identified. Through holes 134 are dimensioned so that the associated drive link foot 132 can seat around the adjacent saw head drive pins 44. Each drive link 130 is shaped so that foot 132 has a thickness that is greater than the thickness of the metal strip forming the main body of the link. The thickness of feet 132 is typically no greater than the thickness of the guide bar 62.

Two fingers 138, one identified in each of FIGS. 2 and 3, extend distally forward from the distal end of the main body of each drive link 130, one finger identified. Fingers 138 overlap and are spaced apart from each other. More particularly, fingers 138 are spaced apart from each a sufficient distance so that a blade foot 152 can seat between each pair of fingers. Each finger 138 is formed with a hole 140, one hole 140 identified in FIG. 3. The holes 140 of each pair of fingers 138 are in registration with each other.

As part of the process of assembling cartridge 60 of this invention, the blade 150 is positioned so that each blade foot 152 is disposed between a pair of drive link fingers 138. A pin 142, one pin identified, that extends through the finger holes 140 and the blade foot opening 154 located between the finger holes 140. The pin 142 pivotally holds the foot 152 to the associated drive link 130.

During the assembly of the cartridge 60, the inner plate 110 is initially welded or otherwise secured to the bottom plate 88 or to the top plate 124. After this operation is completed, the drive links-and-blade assembly is positioned so that the drive links 130 are seated in the elongated spaces on either side of the inner tine 110. The curved proximally directed face 156 of blade 150 is seated against the curved distally directed face of head 114 integral with the inner tine 110. The top plate 124 or bottom plate 88 is then welded or otherwise secured to the exposed face of the inner plate 110. At the completion of the process of assembling the cartridge 60, the drive link feet 132 seat in plate openings 90 and 128. The drive link fingers 138 seat in openings 94 and 128 formed, respectively in the guide bar bottom plate 88 and top plate 124.

When the cartridge 60 is assembled, plate 98 extends from the inner face of bottom plate 88, through the opening 162 to the inner face of the top plate 124. Plate 98 provides structural support for the guide bar so as to prevent the bar plates 88 and 124 from collapsing inwardly against the blade 150.

Saw 30 and cartridge 60 are prepared for use by fitting the cartridge 60 is fitted to the saw head 34. As a result of this attachment, each drive pin 44 is seated in a separate one of the holes 134 formed in a drive link foot 132. Coupling rod 36 extends through the overlapping openings 92, 112 and 127 of the cartridge 60. The coupling rod 36 is lowered over the guide bar 62 so the head of the coupling rod (not identified) presses against the surface of inner plate 104 exposed through top plate opening 127. This press action holds the cartridge 60 to the saw head 34. When the cartridge 60 is secured to the drive head, the drive pins 44 and drive links 130 cooperate to urge the blade 150 proximally. The proximally directed face 156 of the blade 150 is urged against the curved face of head 114 internal to the cartridge 60.

Saw 30 is actuated by depressing trigger 46. This results in the actuation of the motor 42. The actuation of the motor 42 results in the back and forth oscillation of the drive pins 44. The drive pins 44 to cause the drive links 130 to engage in opposed back and forth reciprocation of the drive links. The opposed back and forth motion of the drive links 130 causes the blade to pivot back and forth around the head 114 internal to the cartridge. The pivoting action of the blade teeth 168 causes the teeth to cut the tissue against which the cartridge is pressed.

Figure 6:
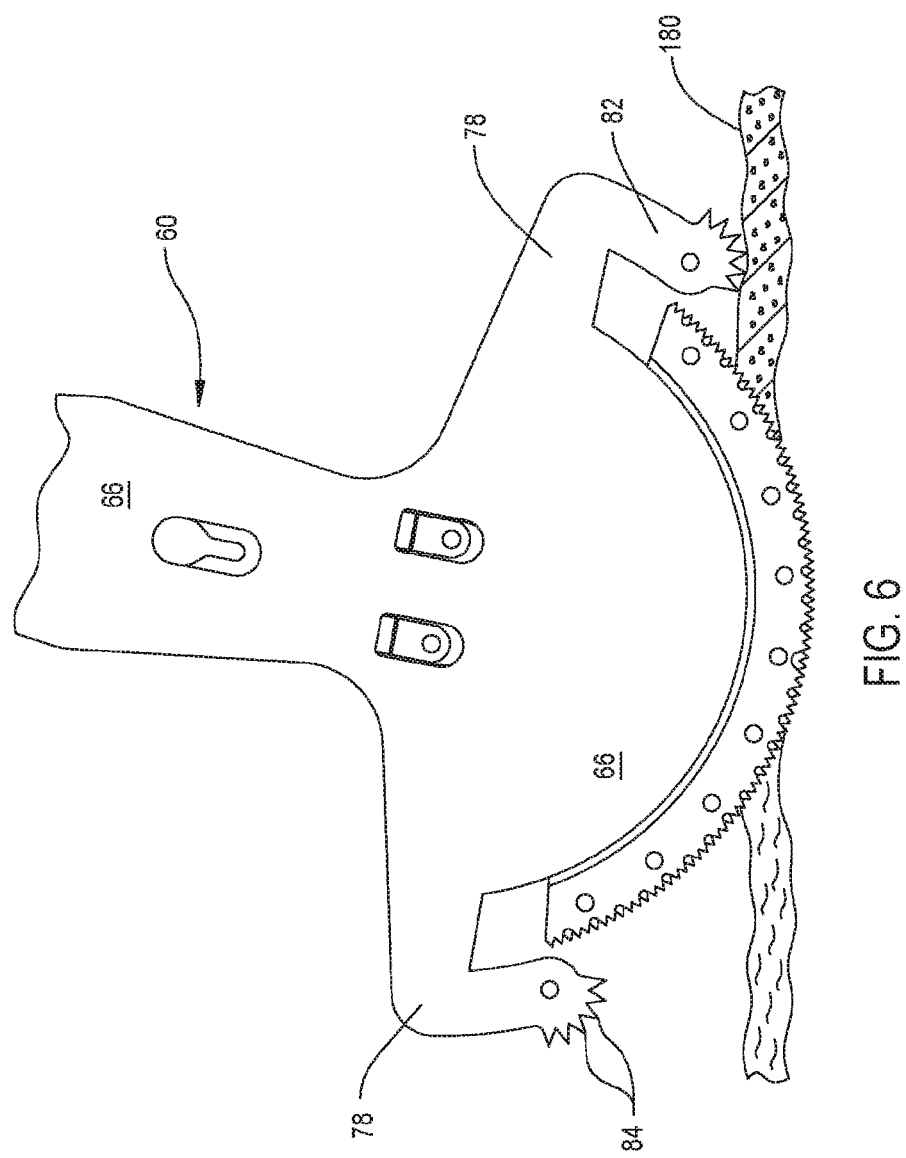
FIG. 6 is a side and partial cross sectional view depicting how a structural component of the guide bar of the cartridge of this invention both functions as a pivot arm.

To cut tissue, typically bone 180, the saw 30 and cartridge 60 are positioned so the teeth 168 of the blade 150 are directed towards the bone as seen in FIG. 6. As part of this process, one of the arms 78 is positioned so the fingers 84 integral with the arm press against an uncut section of the bone. The bone against which the fingers 84 rests functions as the static location around which the arm 78 pivots. Fingers 84 are located to one side of the zone in which the teeth 168 of the blade 150 travels. A portion of the weight of the saw 30 and cartridge 60 is thus transferred through the arm and fingers to the section of the bone against which the fingers are pressed. This reduces weight of the saw and cartridge the surgeon has to overcome in order to control the rate of the plunge of blade 150 into the bone.

Once the saw and cartridge are so positioned, the surgeon pivots the assembly downwardly, into the bone in order to make the desired cut. Once one section of the bone 180 is cut, the cartridge is withdrawn from the cut. The cartridge is repositioned to cut a new section of bone. In FIG. 6 this is seen by the different depiction of the bone to the left and right of the blade 150. To the left of the blade 150, the bone is shown with surface shading. This is represent that this section of the bone has been cut. The right of the blade 150 the bone is depicted as cross hatched. This is to indicate that the bone is not cut and that the right side arm is disposed on top of the bone.

Arm 82 and fingers 84 are thus understood to limit the movement of bar 212, the movement of the whole of cartridge 60 towards the tissue, the bone against which the blade 150 is directed.

II. Second Cartridge

Figure 7:
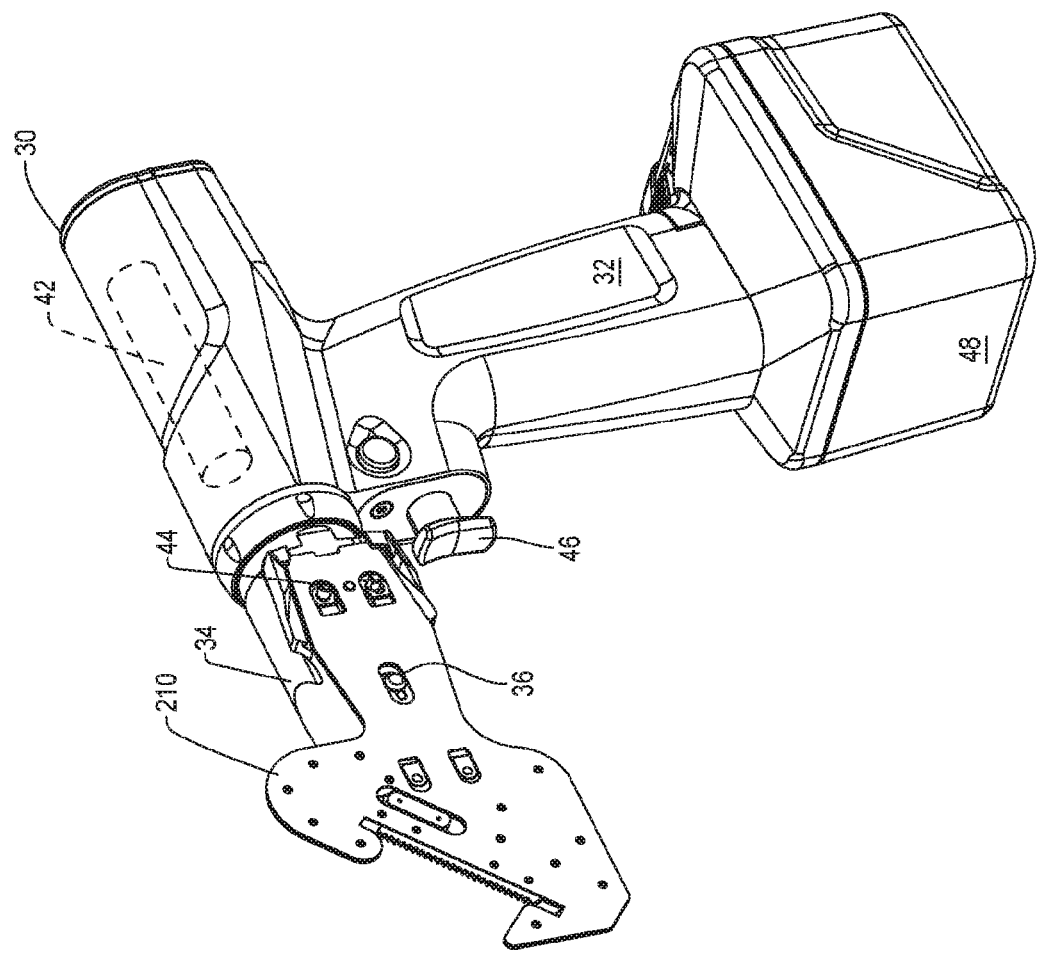
FIG. 7 is a perspective view of a second surgical blade cartridge of this invention attached to the saw.
Figure 8:
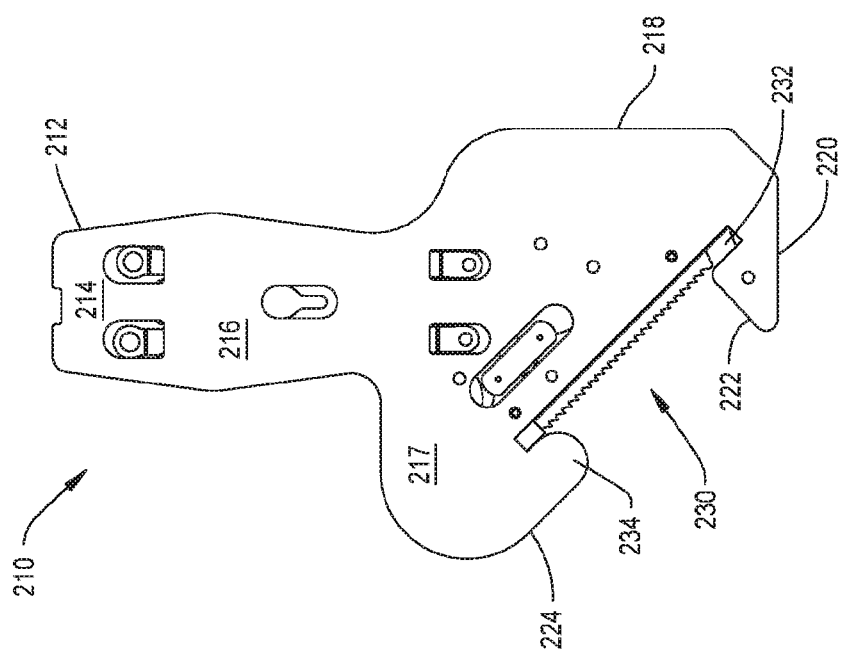
FIG. 8 is side plan view of the cartridge of FIG. 7.
Figure 9:
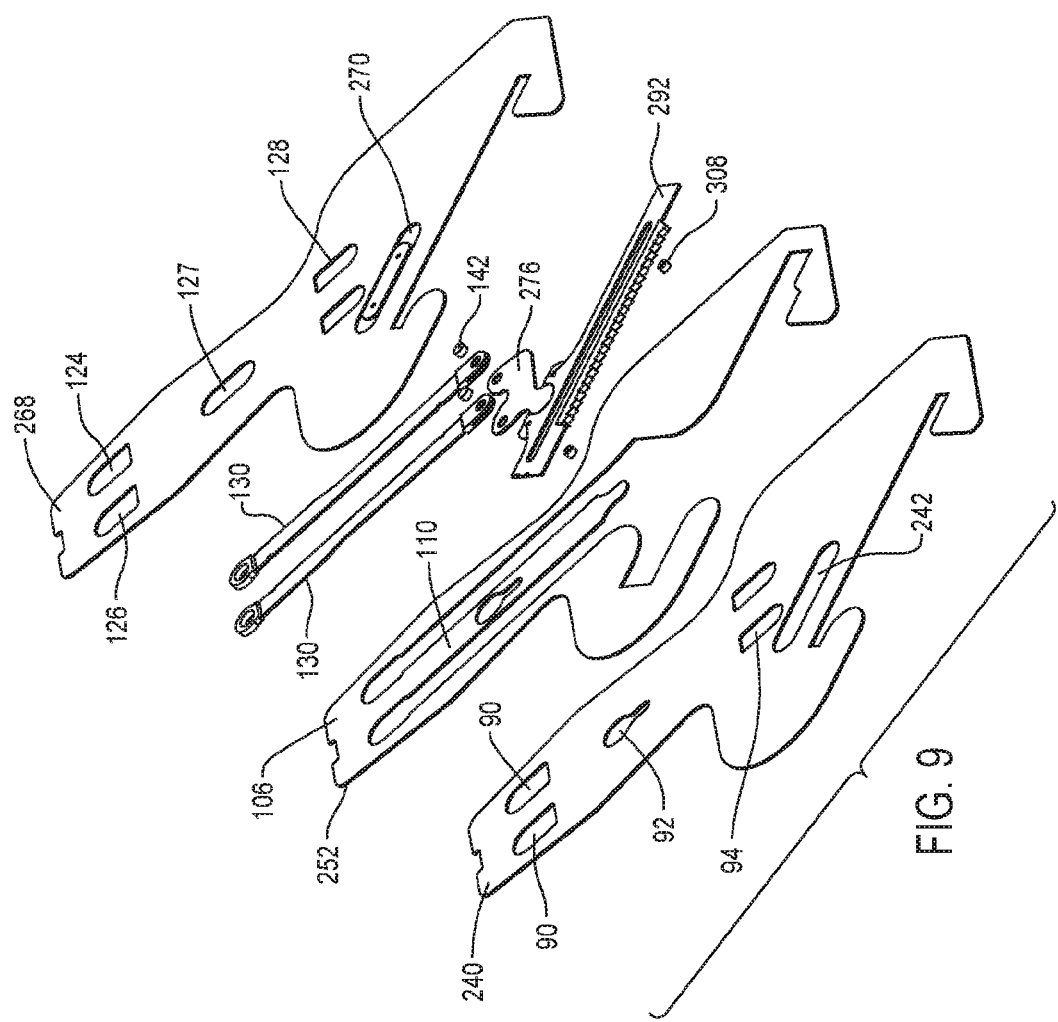
FIG. 9 is an exploded view of the cartridge of FIG. 7.

FIG. 7 illustrates a second cartridge 210 of this invention releasably mounted to the saw 32. Cartridge 210, as seen in FIGS. 8 and 9, includes a guide bar 212 to which a blade 292 is moveably mounted. The previously described drive links 130 are moveably mounted in the guide bar 212. The fingers 138 integral with links 130 are connected to a common pivot link 276. The pivot link 276 is connected to the blade 292. Collectively, the pivot link 276 and the blade 292 are connected together so the oscillation of the pivot link around a point results in the back and forth reciprocation of the blade along a line coincident with the longitudinal axis of the blade. Given that the blade of this version of the invention moves along a linear path of travel, this version of the invention is sometimes referred to as a surgical reciprocating saw blade cartridge.

Guide bar 212 is a laminate structure consisting of a bottom plate 240, an inner plate 252 and a top plate 268. Plates 240, 252 and 268 are formed so the guide bar 212 has a foot 214 is essentially identical to the previously described foot 64. Forward of foot 214, the guide bar has a trunk 216. Trunk 216 is essentially identical in shape to trunk 66.

The guide bar 212 has a head 217 that extends forward from the trunk 216. The head is formed so as to extend laterally outwardly from the sides of the trunk 216. Head 217 is shaped to have a first side 218, the edge of which is identified, that extends along a line that is parallel to the proximal-to-distal longitudinal axis through cartridge 210. At the distal end of the first side 218 the head has a front face 220, the edge of which is identified. The head 217 is shaped so that the front face extends perpendicularly from the first side 218 towards the longitudinal axis of the cartridge. The front face 220 does not extend the whole length of the head. Instead that front face terminates at a location near the longitudinal center axis of the cartridge 210. The head 217 is further formed so that a recessed face 222, the edge of which is identified, extends proximally inward from the free end of the front face. As the recessed face 222 extends inward from the front face, the recessed face extends towards the first side 218.

Opposite the first side 218, the head 217 is formed to have a second side 224. From the proximal end of the head 217, as the second side 224 extends distally, the second side 224 extends inwardly, towards the longitudinal axis of the cartridge. The second side 224 does not extend to the longitudinal axis of the cartridge. Instead, the second side terminates at a curved tab 234.

Tab 234 is spaced away from the opposed recessed face 222 of the head. Thus between face 222 and tab 234 the head is formed to have a notch 230. The head 217 is formed so that the major axis through notch 230 is along a line that is angled relative to the longitudinal axis of the cartridge 210. The head 217 is further formed so that notch 230 opens into a slot 232 that extends through the head, from the outer face of the bottom plate 240, the inner plate 252 and to the outer face of the top plate 268. Slot 232 has a major axis that is parallel to the major axis of notch 230. Slot 232 is longer in length than the notch 230. Thus, slot 232 separates the proximal end of recessed surface 222 from the rest of the head 217. Slot 232 also separates tab 234 from the portion of the head 217 immediately proximal to the tab.

The bottom plate 240 is formed to have the openings 90, the opening 92 and the openings 94 previously described with respect to plate 88. Bottom plate 240 also has an opening 242. Opening 242 is oval shaped. The opening 242 is located between the openings 94 and the portion of the bottom plate 240 that defines slot 232. The bottom plate 240 is shaped so the major axis of the opening 242 is parallel to the major axis of slot 232.

Inner plate 252, seen in FIGS. 9 and 11, is formed to have the base 106 and inner tine 110 of the previously described inner plate 104. At one end of the base 106 a first outer tine 254 extend distally forward. A second outer tine 258 extends distally forward from the opposed ends of base 106. Outer tines 254 and 258 are understood to be parallel to and spaced apart from the inner tine 110.

A first peninsula 256 extends forward the free end of the first outer tine 254. First peninsula 256 is the section of inner plate 252 that forms one side of the inner portion of head 217 of the guide bar 212. A second peninsula 260 extends forward from the free end of the second outer tine 258. Second peninsula is the section of the inner plate 252 that forms the second side of the inner portion of the head 217 of the guide bar. At their distal ends peninsulas 256 and 260 are spaced apart from each other so as to form the center slice section of notch 230. As a result of peninsulas 256 and 260 being spaced apart from each other, the peninsulas 256 and 260 also form the center portion of the center slice section of slot 232. Peninsula 256 is shaped to form an end portion 262 of the center slice section of slot 232, identified in FIG. 11. The end portion 262 of slot 232 extends beyond the ends of the slot defined by the bottom plate 240 and the top plate 268. Peninsula 260 is shaped to form the opposed second end portion 264 of the center slice section of slot 232. This end portion of slot 232 also extends beyond the end portion of the slot defined by plates 240 and 268. These slot end portions 262 and 264 are thus located between the opposed and spaced apart inner face of the bottom plate 240 and the top plate 268.

Top plate 268 has an outer shape that is essentially identical to that of the bottom plate 240. The top plate 268 is formed to have the openings 126, the opening 127 and the openings 128 previously described with respect to plate 124. Top plate 268 has an opening 270. Opening 270 is identical in shape to bottom plate opening 242. When cartridge 210 is assembled, opening 270 is in registration with opening 242

Figure 10:
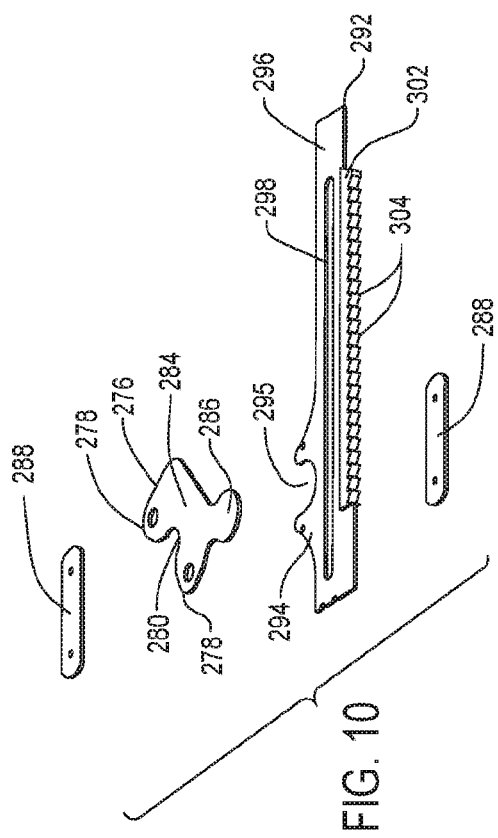
FIG. 10 is an exploded view of the blade and interconnecting link internal to the cartridge of FIG. 7.

The blade 292 as seen in FIG. 10, includes an elongated, rectangularly shaped base 296. Base 296 is dimensioned to seat in slot 232 internal to the guide bar 212. The base 296 has a length that, while less than that of the length of the slot 232 is sufficiently long so that regardless of the position of the base in slot 232, the opposed ends of the base are seated in the opposed end portions 262 and 264 of the slot. Thus the base is able to reciprocate along the longitudinal axis of the axis of slot 232 while the bottom and top plates 240 and 268, respectively, hold the base to the guide bar 212.

Blade 292 is further formed so an elongated slot 298 extends through the opposed faces of the base 296. Slot 298 does not extend to either end of the base 295. As part of the process of assembling of assembling cartridge 210, pins 308 are mounted to the guide bar 212 to extend between the bottom and top plates 240 and 268, respectively. One pin 308 identified in each of FIGS. 9 and 11. Each pin 308 is mounted to the guide bar extend through the slot 298 internal to the blade 292. Not identified are the holes in plates 240 and 268 in which the pins 308 are mounted. The pins 308 stabilize the reciprocal movement of the blade 292 in the slot 232.

A socket 294 extends proximally from the proximally directed end of the base 296. Socket 294 is positioned so that when cartridge 210 is assembled, the socket is located in the void between the opposed peninsulas 256 and 260 of the inner plate 252. The socket 294 is formed to have a circular opening 295. Opening 295 extends inwardly from the proximal end of the socket 294. The blade socket 294 and base 296 are understood to have a common side to side thickness essentially equal to the side to side thickness of the inner plate 252.

The blade 292 also has a head 302. The head 302 extends distally forward from the distally directed end of the base 296. Head 302 to have the teeth 304 suitable for cutting the tissue against which the blade 292 is applied. The head 302 and, more particularly, teeth 304 have a side to side thickness greater than that of the blade base 296. More specifically, the teeth 304 have a thickness such that the kerf cut by the teeth will be sufficient to accommodate at least the head 217 of the guide bar 212.

When cartridge 210 is assembled, the teeth 304 are located in the portion of the slot 232 immediately adjacent notch 230. Teeth 304 are thus located inwardly of the recessed face 222 and tab 234 of the guide bar 212. As seen in FIG. 11A, each tooth 304 has a rake surface 305 and a clearance surface 307 that extends the from the rake surface 305, (one of each of the rake and clearance surfaces identified.) In the illustrated version of the invention, each rake surface 305 extends along a plane that is perpendicular to the longitudinal axis through the blade 292. Cartridge 210 is constructed so the rake surfaces 305 face recessed face 222 of the guide bar 212. Each clearance surface 307 angles away from the rake surface 305 with which the clearance surface is associated. More particularly, each clearance surface 307 extend both proximally and towards tab 234. The edge where the complementary rake surface 305 and a clearance surface 307 of a tooth 304 meet is the cutting edge 306 of the tooth.

Pivot link 276 is planar in shape. The link 276 has the same thickness as the base 296 of the blade 202 so the link can move in the void between the bottom and top plates 240 and 268, respectively, of the guide bar 212. The pivot link has a base 284. The base is dimensioned to move within the space between the two peninsulas 256 and 260. Two spaced apart feet 278 extend proximally from the base 284. Feet 278 are analogous in shape and function to feet 152 of blade 150. The pivot link 276 has a proximally directed face 280 between the feet 278. Face 280 is analogues in shape and function to face 156 of blade 150. Previously described pins 142 pivotally hold each foot 278 to the adjacent drive link 130. Not identified are the openings in the feet 278 through which the pins 142 extend.

Also part of the pivot link is a head 286. The head 286 extend forward from the base 284. Head 286 is circular in shape. More particularly, the head 286 is dimensioned to closely fit in and rotate in the control space 295 internal to the socket 294 integral with the blade 292.

A plate 288 is welded or otherwise secure over each exposed face of the socket 294. Each plate 288 is oval in shape. When cartridge 210 is assembled, the components are arranged so the head 286 integral with the pivot link 276 and the surrounding socket 294 integral with the blade are disposed between the openings 242 and 270 in the guide bar 212. Each plate 288 seats in a separate one of the openings. The components are constructed so that each plate 288 can reciprocate longitudinally in the opening in which the plate is seated. Plates 288 retain the head 286 integral with the pivot link 276 in the socket 294 integral with the blade.

Cartridge 210 is readied for use the same basic steps used to ready cartridge 60 for use. Cartridge 210 is attached to the saw 50 so the reciprocation of the drive pins 44 results in the like reciprocation of the drive links 130.

Cartridge 210 is used to cut bone when the bone is especially desirable to ensure the blade does not cut any tissue below the bone. One such procedure in which cartridge 210 is used is a procedure in which it is necessary to cut the sternum. The sternum is the plate like bone in the chest. The sternum covers the heart and lungs. The sternum is cut open in order to access these organs and organs in the chest. To avoid damage to the sternum it is imperative that that blade, when making this cut, not cut below the bone.

Figure 12:
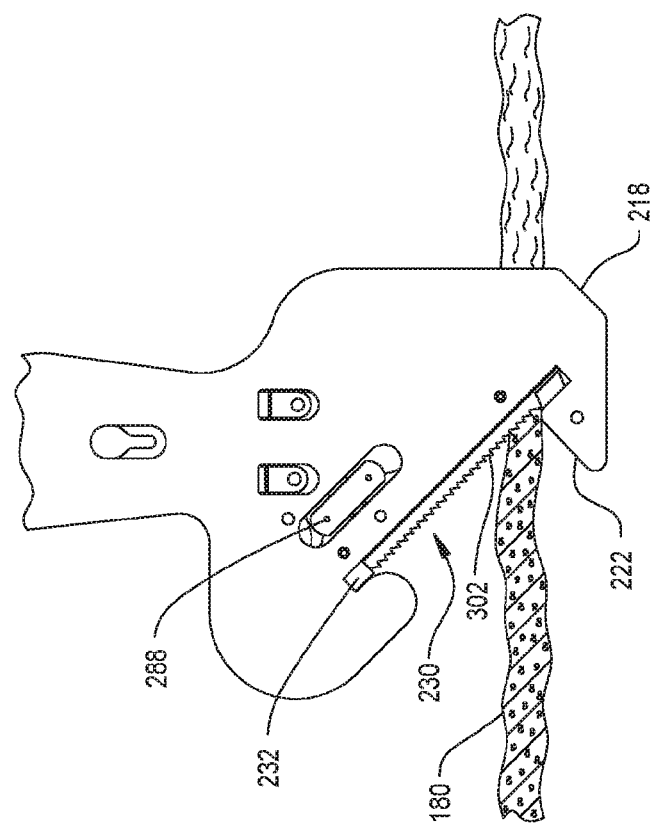
FIG. 12 is a side and partial cross sectional view of how the cartridge of FIG. 7 is used to both cut bone and function as a stop and guard for regulating the depth of the cut.

Cartridge 210 is positioned so the teeth of the blade 292 face the edge of the bone to be cut. As seen in FIG. 12, the cartridge 210 is preferably positioned so that the longitudinal axis through the blade 292 is angled such that section of the blade adjacent guide bar tab 234 leads the section of the blade adjacent recessed surface 222. The cartridge is further positioned so the recessed surface is disposed immediately below the section of bone being cut.

Trigger 46 is depressed to actuate the blade 292. More particularly, the actuation of pins results in the back and forth reciprocation of the drive links 130. The reciprocation of the drive links 130 oscillates the pivot link 276 around head 114 of tine 110. The arcuate oscillation of the pivot link 276 reciprocates the blade 292 back and forth in slot 232.

The reciprocating blade 292 is pressed against the sternum to form the desired cut. The surgeon holding the saw 30 and cartridge exerts a slight upwardly force of the saw so as to hold recessed face 222 against the inner surface of the sternum immediately forward of the moving blade 292. Further, during one-half of a single reciprocating cycle of the blade 292, the blade moves towards the recessed face 222. During this phase of blade motion, the rake surfaces 305 of the teeth grab into the face of the bone being cut. This action, along with the movement of the blade towards the recessed surface 222, results in the blade applying a force against the bone that serves to pull the recessed surface 222 against the inner surface of the sternum. Thus, the cutting action of the cartridge adds to the force the surgeon applies in order to hold recessed surface 222 against the sternum. In FIG. 12 the formation of the cut is depicted by the fact that to the left of the blade head 302, the uncut tissue is depicted in cross section. To the right of the side 218 of the guide bar 212 surface shading shows the face of the cut bone.

This holding of recessed surface 222 of the cartridge 210 against the inner surface of the sternum reduces the likelihood that soft tissue will become trapped between the sternum and the recessed surface. Reducing the incidence of this tissue being so trapped results in a like reduction in the incidence of this tissue being inadvertently cut. Further it should be understood that the portion of the bar 212 that defines surface 222 and that abuts the bone prevents the bar and thus the whole of cartridge 210 from being drawn away from the bone. This ensures that the blade 292 forms a cut that extends between the opposed proximal and distal facing surfaces of the bone.

During the second phase of a reciprocating cycle of the blade 292, the blade moves from the recessed surface 222 towards tab 234. In this phase of the cycle, the clearance surfaces 307 of the teeth move past the tissue. Owing to the geometry of the teeth, the clearance surfaces 307 only rub against tissue. Thus, this motion of the blade does not drive the guide bar so the section of guide bar 21 that defines end portion 262 of slot 232 is driven into the soft tissue that underlies the sternum.

Thus cartridge 210 of this invention is designed to substantially eliminate the possibility that the moving blade 292 will press against tissue and organs below the sternum not intended to be cut.

This invention eliminates the need to some instances have a sternum saw ready for use. As implied by its name, a sternum saw is a saw with features to ensure that, when the blade of the saw is applied to the sternum, the blade cuts through the sternum and is not applied against the issue and organs below this bone. Eliminating the need to provide this custom saw can reduces the expenses associated with performing a procedure on a patient when a part of the procedure involves cutting the sternum.

A further feature of this version of the invention is that the section of the head 217 of guide bar 210 that follows the blade 292 into the sternum is relatively long, often greater than 1 cm in length. Owing to this section of the guide bar having a relatively long length, when this section of the guide bar enters the cut, this section of the guide bar essentially block the guide bar from moving outside of the plane of the cut being formed by the cartridge 210. This ensures that cut formed by the guide bar is relatively straight.

III. Third Cartridge

Figure 13:
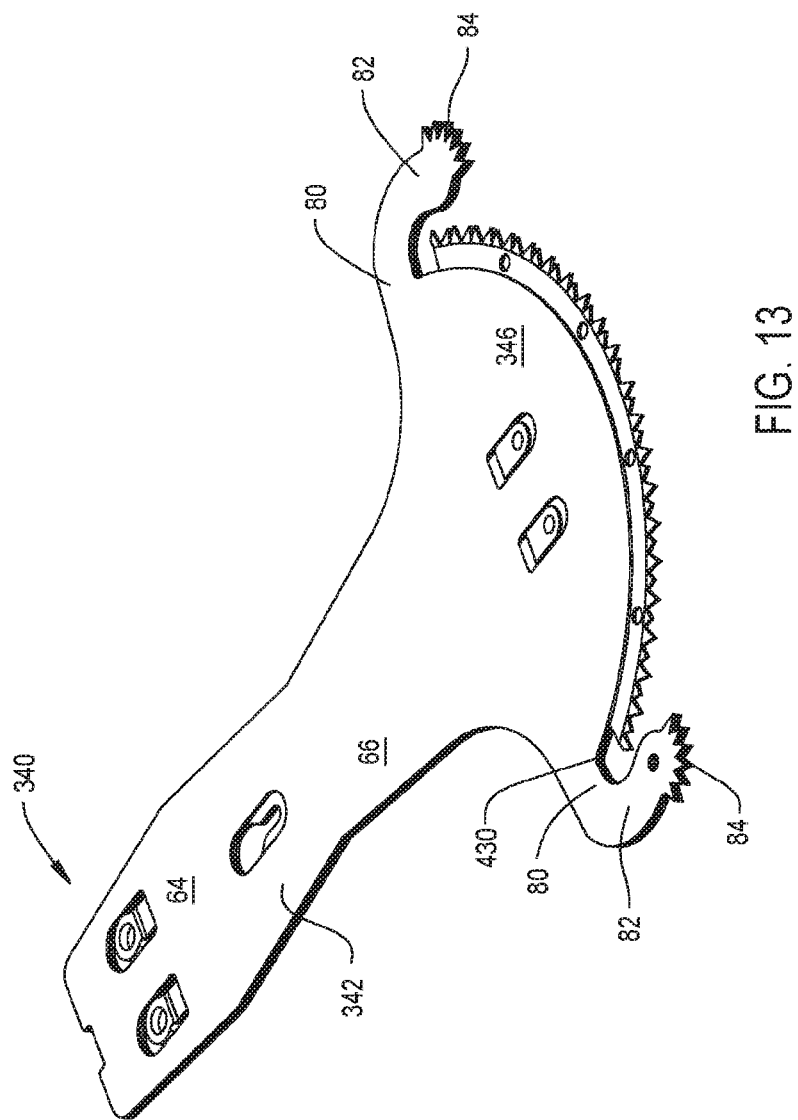
FIG. 13 is a perspective view of a third surgical blade cartridge of this invention.
Figure 14:
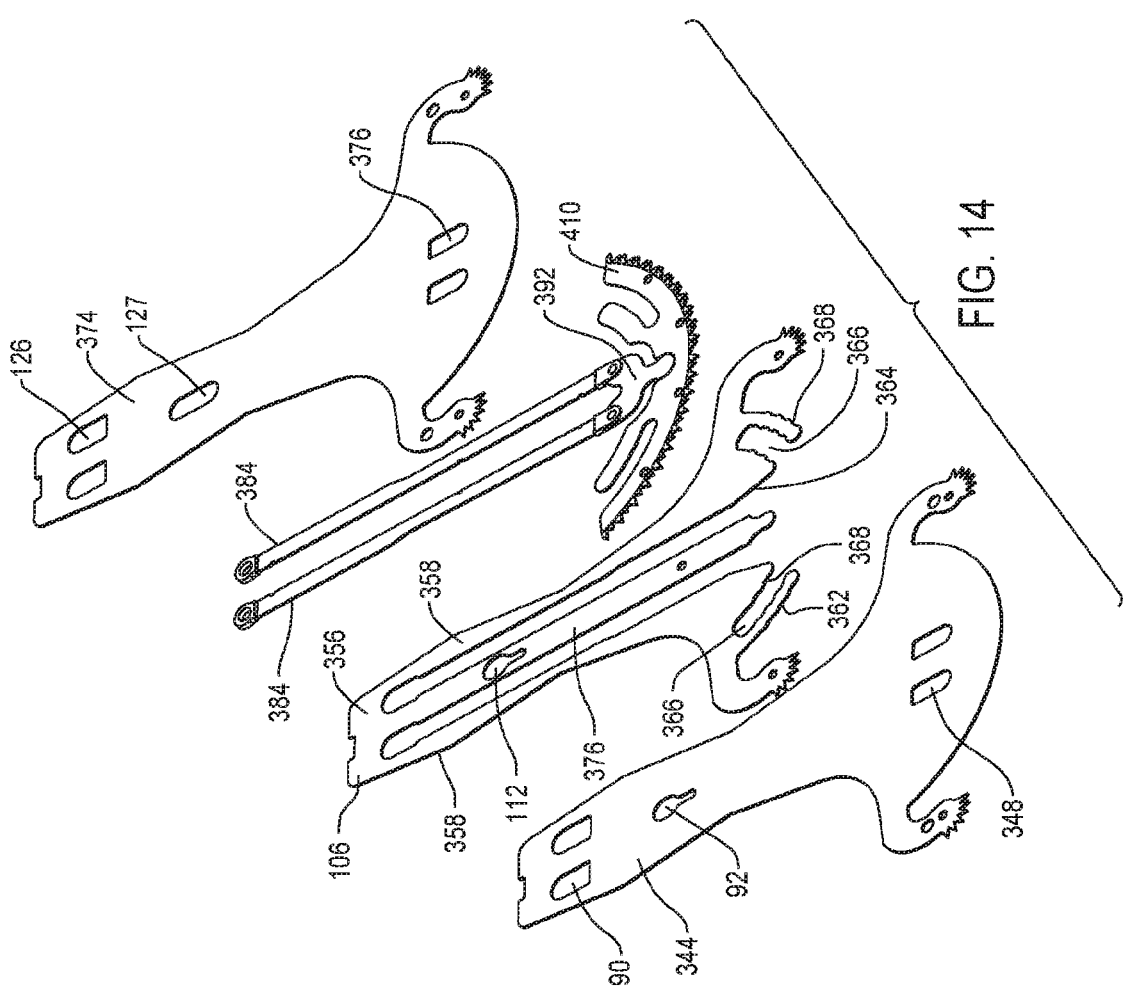
FIG. 14 is an exploded view of the cartridge of FIG. 13.

FIGS. 13 and 14 illustrate an alternative sagittal blade cartridge 340 of this invention. Cartridge 340 includes a guide bar 342 to which a blade 410 is pivotally mounted. Cartridge 340, is shaped to be releasably attached to saw 32.

Guide bar 342 includes a bottom plate 344, an inner plate 356 and a top plate 374. Collectively, the plates 344, 380 and 374 forming the guide bar 342 are shaped so the bar has the foot 64 and trunk 66 of cartridge 60. Bottom plate 344 is thus formed with openings 90 and 92. The top plate 374 is formed with openings 126 and 127. The bottom and top plates 344 and 374, respectively, of guide bar 342 are formed to define head 346 of the guide bar. Head 346 is similar in shape to head 68 of cartridge 60. A difference between the two cartridges is that bottom and top plates 344 and 374, respectively, are formed to defining, respectively two openings 348 and 376, one of each opening identified. The bottom plate openings 348 are analogues to openings 94 integral with cartridge 60. The top plate openings 376 are analogues to openings 128 integral with cartridge 60.

Guide bar 342 is formed to have the shoulders 80, forearms 82 and fingers 84 integral with cartridge 60.

Figure 16:
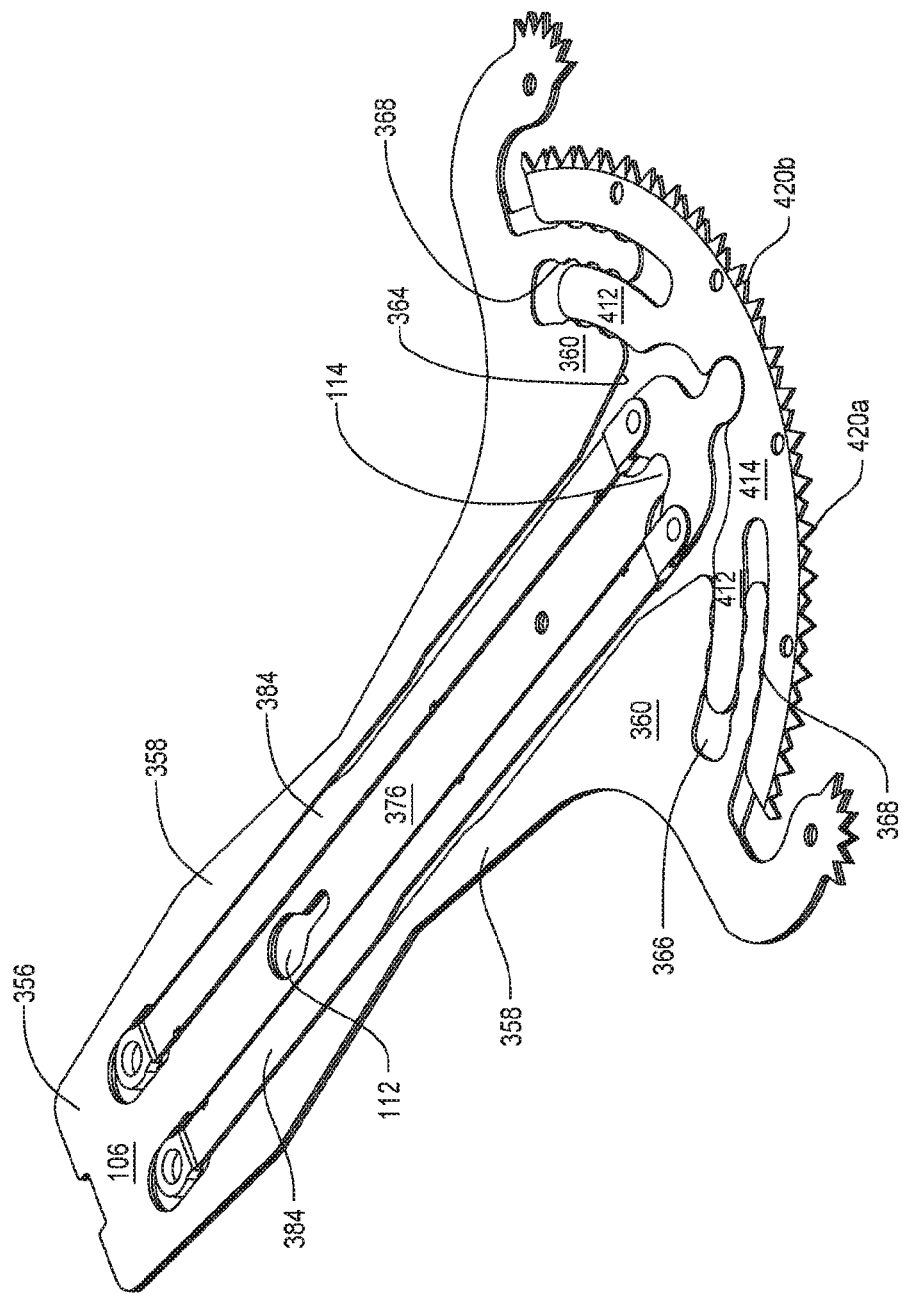
FIG. 16 is a perspective view of the cartridge of FIG. 13 with the top plate removed.

Inner plate 356, the features of which are best seen in FIGS. 14 and 16, has the base 106 common to the above-described cartridges 60 and 210 of this invention. Two outer tines 358 and an inner tine 376 extend distally forward from the base 106. Each outer tine 358 has a proximal section similar in shape to the proximal section of the tines 108. At the distal end of the proximal section of the tine 358, each tine is shaped to form a land 360. Each land 360 is formed so as to have a distally directed face 362, (one face identified), that is arcuate in shape. The distal faces 362 of the two tines 358 are located on a single arc. Collectively, the components forming the guide bar 342 are constructed so that the distal faces 362 of inner plate 356 are spaced inwardly of the adjacent distally directed faces of bottom plate 344 and top plate 374. Consequently, when the plates are assembled to form the guide bar, a slot 430 extends inwardly from and between the distal ends of bottom plate 344 and the top plate 374. The opening into slot 430 is identified in FIG. 13.

Each outer tine 358 is further forward to have an inwardly directed face 364 (one face identifies). The inwardly directed faces 364 of the two tines 358 are directed towards each other. Lands 360 are further formed so that as each face 362 extends proximally from the distal end of the land, the face angles inwardly toward the longitudinal center axis through the plate 356. Thus, between the lands 360 there is a gap, (gap not identified). Extending proximally from the distal ends of the lands 360, the width across this gap decreases.

Each land 360 is further formed to define a slot 366. Each slot 366 extends inwardly from the inner face 364 of the land 360 in which the slot is formed. Each slot 366 is arcuate in shape. More specifically, as each slot 366 extends away the longitudinal axis of the inner plate 356, the slot curves towards the proximal end of the plate. Each land 360 is further formed to define plural ribs 368, two ribs identified. Inner plate 356 is formed so that the ribs 368 extend inwardly from the opposed faces of each land 360 that define each slot 366. The inner plate 356 is also formed so that the ribs 368 extend outwardly from the distally directed face 362 of each land.

The section of each tine 358 that is part of the shoulder 80-forearm 82-finger 84 section of the tine 358 extends outwardly from the side edge of the land 360.

Inner tine 376 of the inner plate 356 is similar in shape to the previously described inner tine 110. Inner tine 376 is formed to have the previously described openings 112 and head 114. The most significant difference between the inner tines is that inner tine 376 is longer than inner tine 110. More specifically, the inner plate 356 is shaped so the tine head 114 is located in the proximal portion of the gap between the opposed tapered inwardly directed faces 362 of lands 360.

Figure 15:
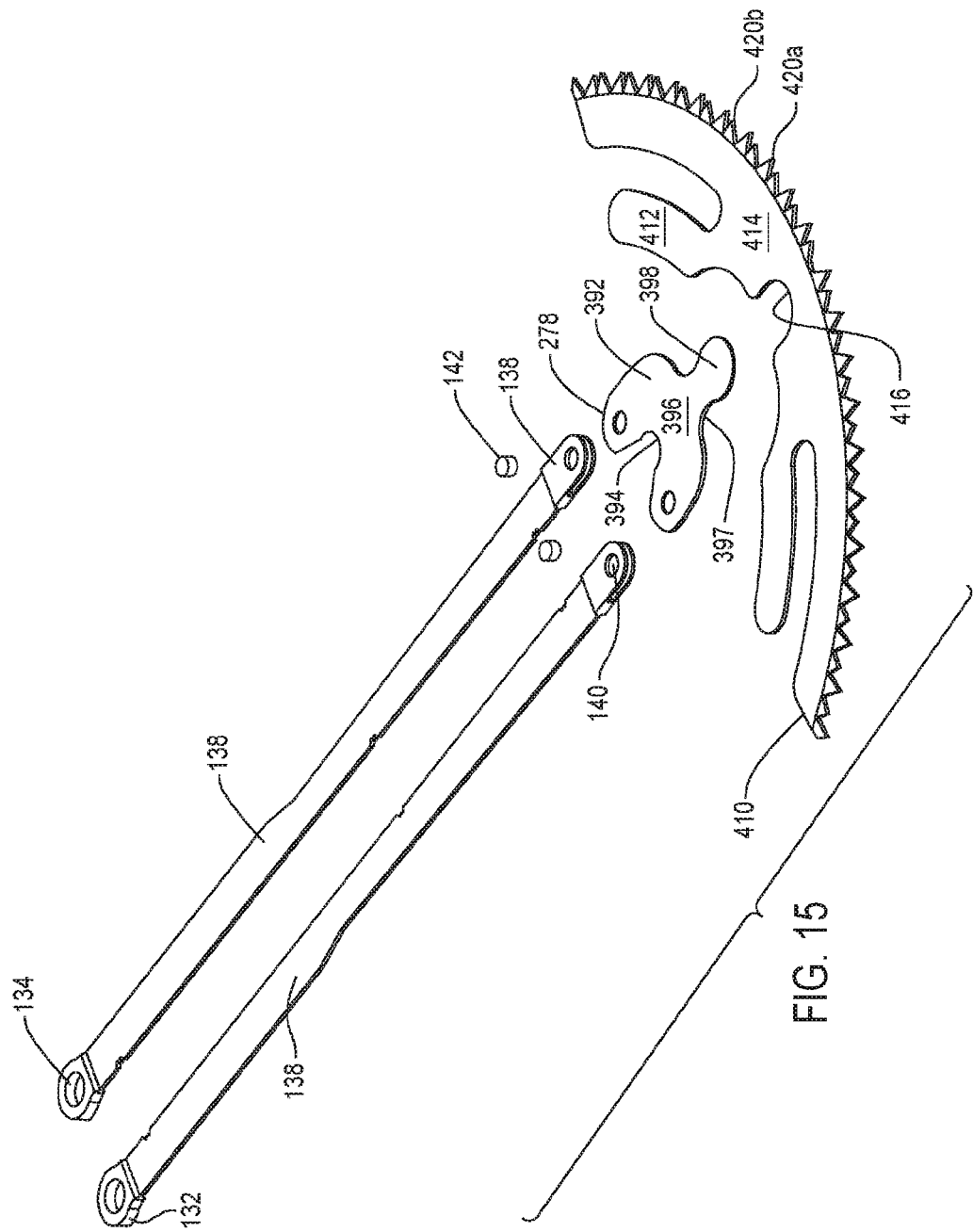
FIG. 15 is an exploded view of the drive link-and-blade sub-assembly of the cartridge of FIG. 13.

Two drive links 384, best seen in FIG. 15, are disposed in the guide bar 342. The drive links 384 are similar in shape to the previously described drive links 130. The only difference between the drive links is that drive links 384 are longer in length than drive links 130. Thus it should be understood that when cartridge 340 is assembled, the fingers 138 integral with drive links 384 seat in the openings 348 and 376 formed in the guide bar 342.

A pivot link 392 is pivotally attached to the fingers integral with the drive links 384. Pivot link 392 includes a base 396. The feet 278 integral with the previously described pivot link 276 extend proximally from the base 396. A curved distally directed face 394, analogues to face 280 is located between the feet. Face 394 is the surface of the link that presses against the head 114 of tine 376.

Pivot link 392 is further formed to have a head 398 that extends distally forward from the base 396. Head 398 is circularly shaped. A neck 397, connects the head 398 to the base. The pivot link is formed so neck 397 has a side-to-side width less than the diameter of head 398/

Blade 410 is formed so as to have an arcuately shaped beam 414. Beam 414 is shaped to seat in and oscillate in slot 430 internal to the guide bar 342. Thus beam 414 subtends an arc less than the arc of guide bar slot 430. The beam 414 is formed to have in the center a notch 416. Notch 416 extends distally forward from the proximal end of the beam 414. The notch is centered on the midline of the beam. The notch 416 is shaped to receive head 398 of the pivot link 392. In many preferred versions of the invention notch 416 is U-shaped.

The blade 410 is formed so as to have two legs 412. The legs extend outwardly and proximally from the beam on the opposed sides of notch 416. Legs 412 and beam 414 can collectively be considered the base of blade 410. Each leg 412 extends outwardly away from the proximal to distal longitudinally axis of the cartridge. As each leg 412 extends away from the longitudinal axis of the cartridge 340, the leg curves proximally. More specifically the components of cartridge 340 are formed so that the opposed proximal and distally directed faces of the legs will seat against the crests of the ribs 368 that protrude in the slots 366. When the blade 410 is so seated, the curved proximally directed faces of beam 414 rest against the crests of the ribs 368 that project forward of the front face of the lands 360. Each leg 412 is further understood subtends an arc less than the arc subtended by the slot 366 in which the leg is seated. The seating of the legs 412 in the slots 366 internal to the guide bar 342 is what retains the blade 410 in the guide bar. The relative dimensioning of the components of cartridge 340 allows the legs 412 to oscillate in the slots 366.

Blade 410 is further formed so as to have teeth 420 that project forward from the distally directed face of the beam 414. In the illustrated version of the invention, the teeth are set. This means the teeth are angled so as to extend out of the plane of the blade 410. In the illustrated version of the invention some teeth, one identified as tooth 420a, are angled so as to extend into the planes of FIGS. 15 and 16. Other teeth, one identified as tooth 420b, are angled so as to extend out of the plane of FIGS. 15 and 16. The set of the teeth 420a, 420b is such that the kerf cut by the teeth is of sufficient width that at least the head of the guide bar can be received in the kerf.

When the cartridge 340 is assembled, each drive link 384 is located in the elongated space between the inner tine 376 and one of the outer tines 358. Pins 142, one identified in FIG. 15, connect each drive link 384 to a foot of the pivot link 392. Head 398 of the pivot link 392 seats in the proximally opening notch 416 of the blade 410.

Cartridge 340 operates in the same general manner and is used in the same general way as cartridge 60 of this invention. The reciprocation of the drive links 138, oscillates the pivot link 392 in an arc centered on the head 114 of the inner tine 376. The oscillatory movement of the pivot link 392 is transferred through head 398 to the blade 410. The blade 410 thus engages in a back and forth oscillation in an arc centered on the head 114 of the inner tine 376. In many versions of the invention, cartridge 340 is constructed so in the blade 410 is able to pivot between 3 and 10° either side of the longitudinal axis through guide bar 362. It should be understood that when cartridge 340 is actuated, there is some relative motion between the pivot link 392 and the blade 410.

A difference between the two cartridges 60 and 340 is that for having an arcuate set of teeth with the same radius and that subtends the same arc, blade 410 of cartridge 340 has a smaller mass than the mass of blade 150 of cartridge 60. A second difference between the two blades concerns the points around which the blades oscillate. Blade 150 pivots around the center of tine head 114. Blade 410 rotates around center point of the arc on which slots 366 are centered. This point, while on tine 110, is located proximal to the center of tine head 114. A benefit of blade 410 having this reduced mass and proximally displaced center of oscillation is that vibratory forces produced by blade 410 are less than that produced when blade 150 is oscillated. This means that, when actuated, cartridge 340 vibrates less than cartridge 60.

The reason blade 410 rotates around a center point proximal to the center of head 114 internal to blade bar 34 is due to how the blade 410 is connected to drive links 130. The drive links 130 are not physically attached to the blade 410. Instead, drive links 130 are through pivot link 392, connected to blade 410. Further, pivot link 392 are not simply connected together so that the pivot link is only able to rotate in notch 416 internal to the blade. Owing to the shape of the head 398 of the pivot link and notch 416, the head is able to both pivot in the notch and engage in some minor longitudinal movement within the notch. The ability of the pivot link 392 and blade 410 to engage in this movement relative to each other is what results in the blade 410 moving around a pivot point that is spaced proximally from the center of the tine head 114.

IV. Fourth Embodiment

Figure 17:
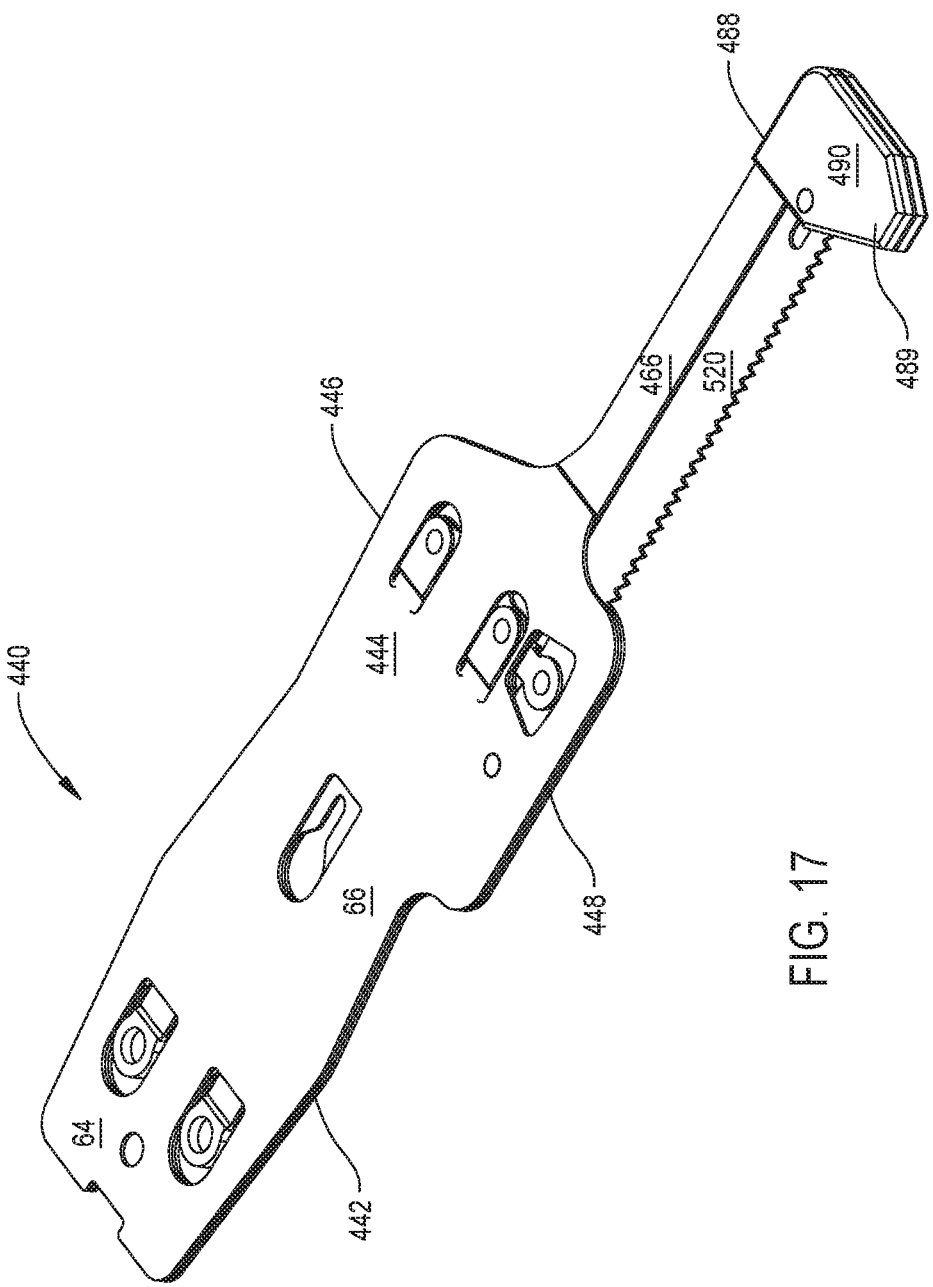
FIG. 17 is a perspective view of a fourth surgical blade cartridge of this invention.

An alternative cartridge, specifically a sternum cartridge 440 of this invention is initially described by reference to FIGS. 17 and 18. Cartridge 440 is referred to as a sternum cartridge because this cartridge is designed to cut the sternum while limiting the cutting of the tissue below the sternum. The cartridge 440 includes a guide bar 442. A distal foot 488 is integrally attached to and located forward of the guide bar 442. A blade 520, also part of the cartridge 440 extends between guide bar 442 and distal foot 488. The blade 520 is moveably mounted to the guide bar 442 and foot 488 so as to engage in reciprocal movement between the guide bar and the foot.

Guide bar 442 is a laminate structure that includes a bottom plate 450, an inner plate 460 and a top plate 480. Collectively, the plates 450, 460 and 480 are shaped so that guide bar 442 has the foot 64 and torso 66 of the previously described guide bars. To distinguish the foot 64 from the distal foot 488, foot 64 will be referred to as the proximal foot 64 of the guide bar 442. Plates 450, 460 and 480 are further formed so that guide bar 442 has a head 444. The guide bar 442 is shaped so that on one side, the left side of the bar when viewed from the proximal end of the bar in FIG. 17, the head has a side face 446, the edge of which is identified. Guide bar 442 is formed so that extending distally from the torso 66, the side face 446 tapers outwardly from the longitudinal axis along the guide bar. On the opposed side of the head 444, guide bar 442 has a side face 448. The head is formed so that the side face is located outwardly from the adjacent narrow width portion of the torso 66. The guide bar is further formed so that the side face 448 extends along a line that is parallel to the longitudinal axis of the longitudinal axis along the guide bar 442.

The bottom plate 450 is formed to have the openings 90 and 92 common to the previously described bottom plates. The previously described openings 94 are formed in the section of the bottom plate 450 that defines the head 444 of the guide bar 442. An additional opening 452 is also formed in bottom plate 450. The bottom plate 450 is formed so that opening 452 is located between the opening 94 closest to the portion of the plate that forms the side face 448 and the side face 448. The bottom plate is formed so opening 452 is arcuate and shape and centered along a curve that would be located outwardly of side face 446 of the guide bar 442. Proximal to opening 452, the bottom plate 450 is formed to have a through hole 454.

Bottom plate 450 is further formed to have a nose 456. Nose 456 extends distally forward from the portion of the bottom plate 450 that is slightly offset from the center of the guide bar 442. More particularly, the nose 456 extends forward from a location that is slightly closer to side face 448 of the guide bar than side face 446.

Figure 18:
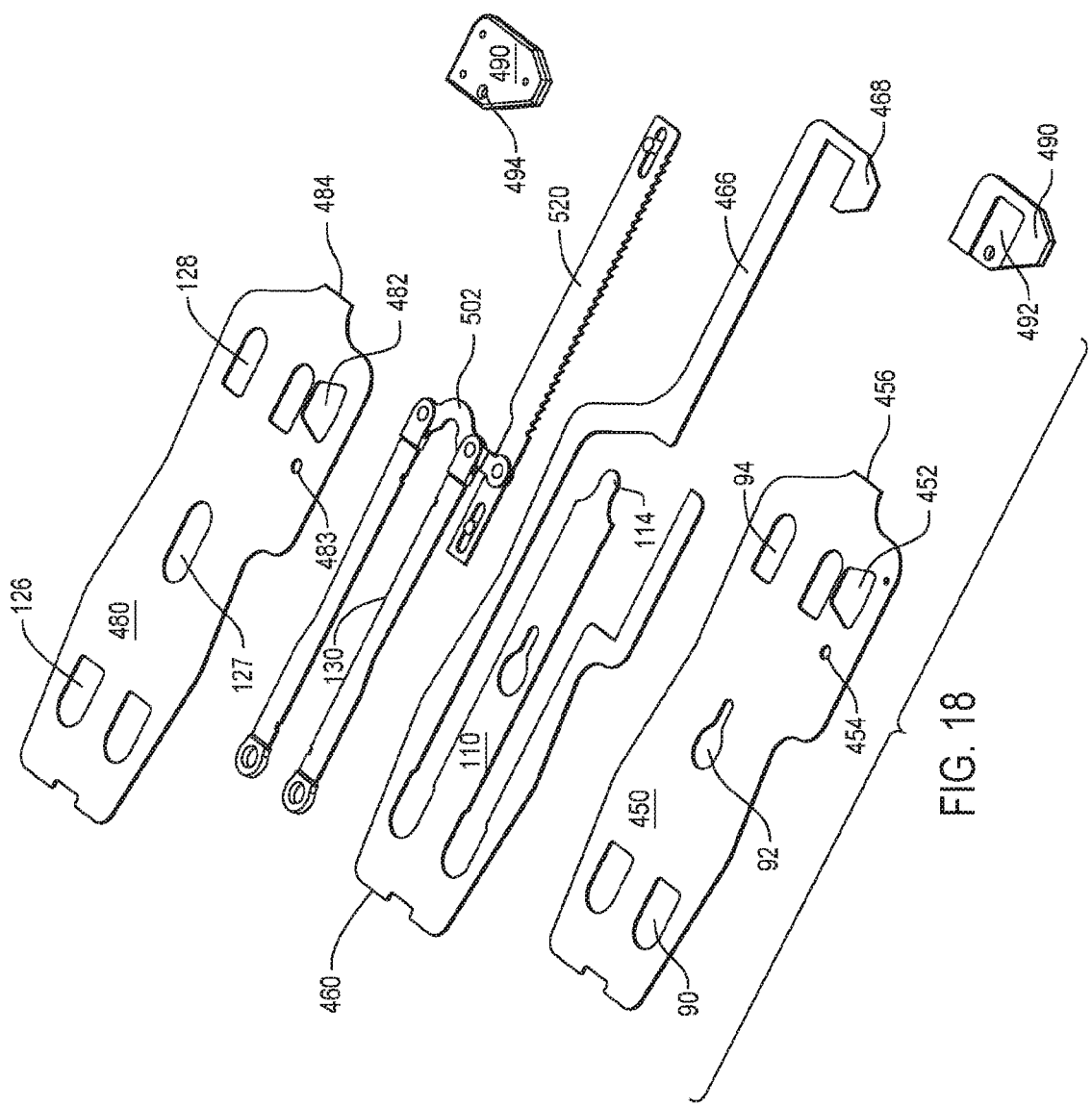
FIG. 18 is an exploded view of the cartridge of FIG. 17.
Figure 20:
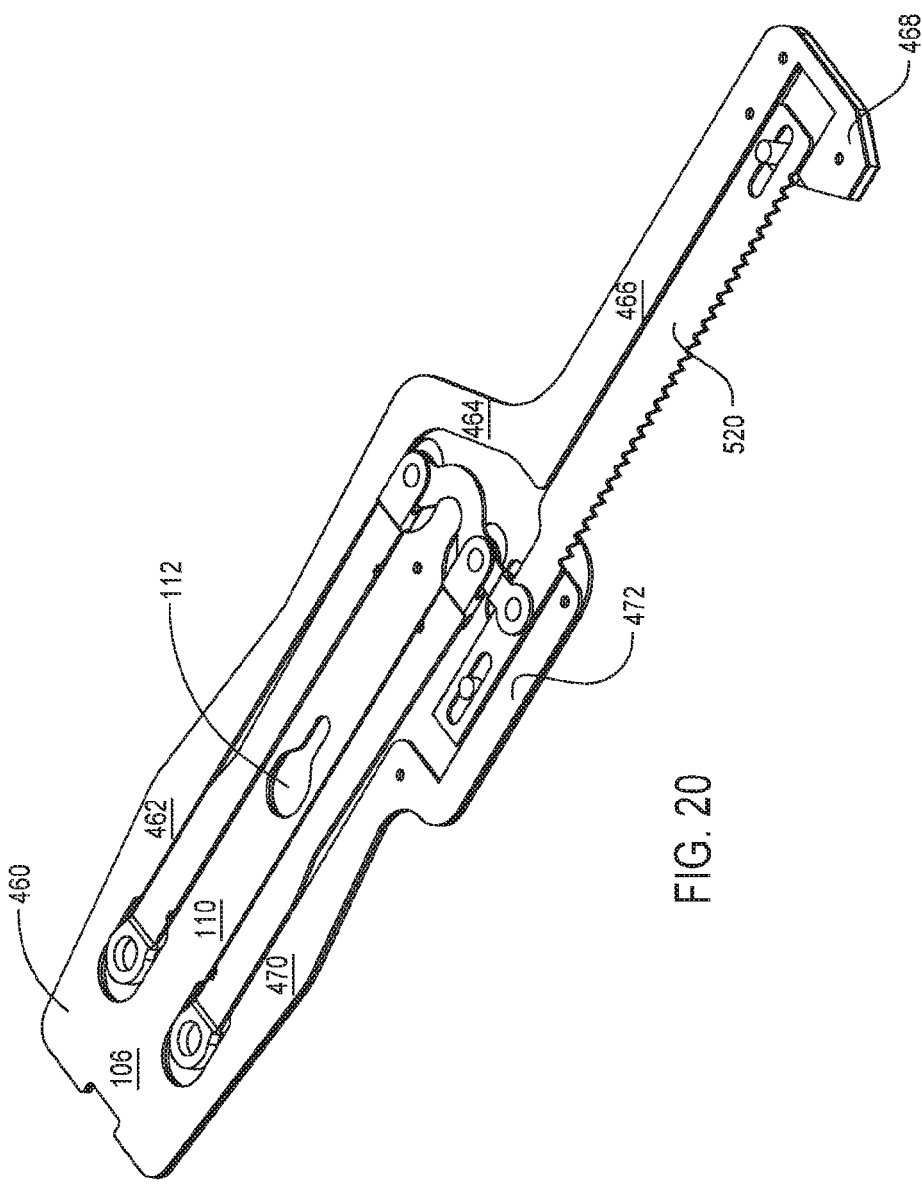
FIG. 20 is a perspective view of the cartridge of FIG. 17 with the top plate removed.

Inner plate 460, as seen in FIGS. 18 and 20, has the base 106 common to the previously described inner plates. The previously described inner tine 110 extends forward from the center of the base 106 of plate 460. An outer tine 462 extends forward from left end of base 106 of inner plate 460. Tine 462 is essentially identical in shape to the corresponding outer tine 108 of inner plate 104. The inner plate 460 is further formed so a proximal beam 464 and a distal beam 466 extend forward from tine 462. Proximal beam 464 is the structural member of the inner plate that actually extends forward from the free end of the tine 462. The inner plate 460 is formed so that as the proximal beam extends forward the beam 464 extends inwardly. More particularly, beam 464 extends to the space between the noses 456 and 484 of the bottom and top plates 450 and 480, respectively. Distal beam 466 extends distally forward from the free end of the proximal beam 464. The inner plate 460 is formed so the longitudinal axis of the distal beam 466 is laterally offset from and parallel to the longitudinal axis through the guide bar 452.

An L-shaped arm 468 extends laterally from one side of the distal beam 466 adjacent the distal end of the beam 466. Arm 468 is directed towards side face 448 of the guide bar 442. The inner plate is further formed so that the outer section of arm 468, in addition to being parallel to and spaced away from beam 466, extends proximally inward, towards the head 444 of the guide bar 442.

Inner plate 460 is formed so a second outer tine, tine 470 extends distally forward from the end of base 106 opposite the end of the base from which outer tine 462 extends. The proximal section of outer tine 470 has a shape similar to that of the proximal section of tine 108. Outer tine 470 is further formed so as to have distal section, section 472, that is located laterally away from the proximal section. The outer tine 470 is formed so that the distal section 472 is located laterally outwardly the base 106 of inner plate 460. In the illustrated version of the invention, the inner plate 460 is formed so distal section 472 extends outwardly from the rest of the tine 472 at a location forward of where the opening 112 is in the inner tine 110. Both outer tines 462 and 470 are spaced away from the inner tine 110. Not identified are the spaces between the tines. Owing to the outward spacing of the distal section 472 of outer tine 470, the width of the space between the distal section 472 of the outer tine 470 and the inner tine 110 is greater than the width of the space between the proximal section of the outer tine 470 and the inner tine 110.

The top plate 480 is formed to have the openings 126 and 127 common to the previously described top plates. The previously described openings 128 are formed in the section of the top plate 480 that is part of the head 444 of the guide bar 442. Top plate 480 is also formed to have an opening 482. Opening 482 is identical in shape to opening 452 of the bottom plate 450. A hole 483 is also formed in the top plate 480. Hole 483 is identical to bottom plate hole 454. When the guide bar 442 is assembled, the top plate opening 482 is in registration with the bottom plate opening 452 and hole 483 is in registration with hole 454.

Top plate 480 is further formed to have a nose 484 similar to nose 456 of the bottom plate 450. It should thus be appreciated that when the guide bar 442 is assembled, noses 456 and 484 are in registration and the distal beam 466 extends forward from the space between the noses.

The distalmost section of distal beam 466 and the arm 468 integral with the beam 466 serve as the center component of distal foot 488. An end plate 490 is disposed over each arm 468 and the adjacent portion of the distal beam 466. Thus the distal foot 488 is a laminate sub-assembly that consists of the two end plates 490 and the sections of the distal beam 466 and arm 468 disposed between the end plates. The end plates 490 are shaped to extend over the whole of the arm 468 and the distal section of beam 466. The distal foot 488 thus has a side-to-side thickness greater than that of the adjacent distal beam 466. In some versions of the invention the components forming cartridge 440 are dimensioned so that side to side thickness of the distal foot 488 is greater than that of the guide bar 442. Each end plate 490 is formed with a notch 492, one seen in FIG. 18. Each end plate 490 is formed so the notch 492 extends distally from the proximal end of the plate and opens inwardly from the face of the plate that abuts the beam 466 and arm 468. The notches 492 subtend the three-sided space defined by distal section of the distal beam 466 and arm 468.

Each end plate 490 is formed with a hole 494, one hole 494 identified, that extends between the major faces of the plate. Each hole 494 opens into the portion of the plate 490 that defines the base of the notch 492. When cartridge 440 is assembled, the individual holes 494 are coaxial and the axis around which the holes are centered extends through the three-sided space defined by distal section of the distal beam 466 and arm 468.

It is further observed that the components forming the distal foot 488 are shaped so the foot has a toe 489. Toe 489 is the portion of the foot that projects forward of the below discussed teeth 526 of the blade 520.

Drive links 130 are disposed in the guide bar 442 of cartridge 440. One drive link 130 is located in the space between inner tine 110 and the outer tine 462. The second drive link 130 is located in the space between the inner tine 110 and outer tine 470.

The distal ends of the drive links 130 are connected to a pivot link 502 also disposed in the guide bar 442. The pivot link 502, as seen best in FIG. 19, includes a U-shaped beam 504. Beam 504 has a width that allows the beam to seat within the fingers 138 of the drive links 130. The center section of the beam 504 has a curved U-shaped, proximally directed face 506. When cartridge 440 is assembled, face 506 is the surface of the beam that presses against and pivots around the head 114 of inner tine 110.

Pins 142 pivotally connect the tine fingers 138 to the opposed ends of beam 504. Not seen are the holes in the ends of the beam 504 in which pins 142 are seated.

The pivot link 502 also includes a pair of parallel, spaced apart overlapping fingers 508, one seen. The fingers 508 extend from the end of the beam 504 that is directed towards side face 448 of the guide bar 442. Fingers 508 are similar in shape to the fingers 138 integral with the drive links 130. Not identified are holes that extend through the fingers 508. The components forming the cartridge 440 are arranged so that when the cartridge is assembled, each finger 508 seats in a separate one of openings 452 and 482 formed, respectively in the bottom plate 450 and top plate 480.

Figure 19:
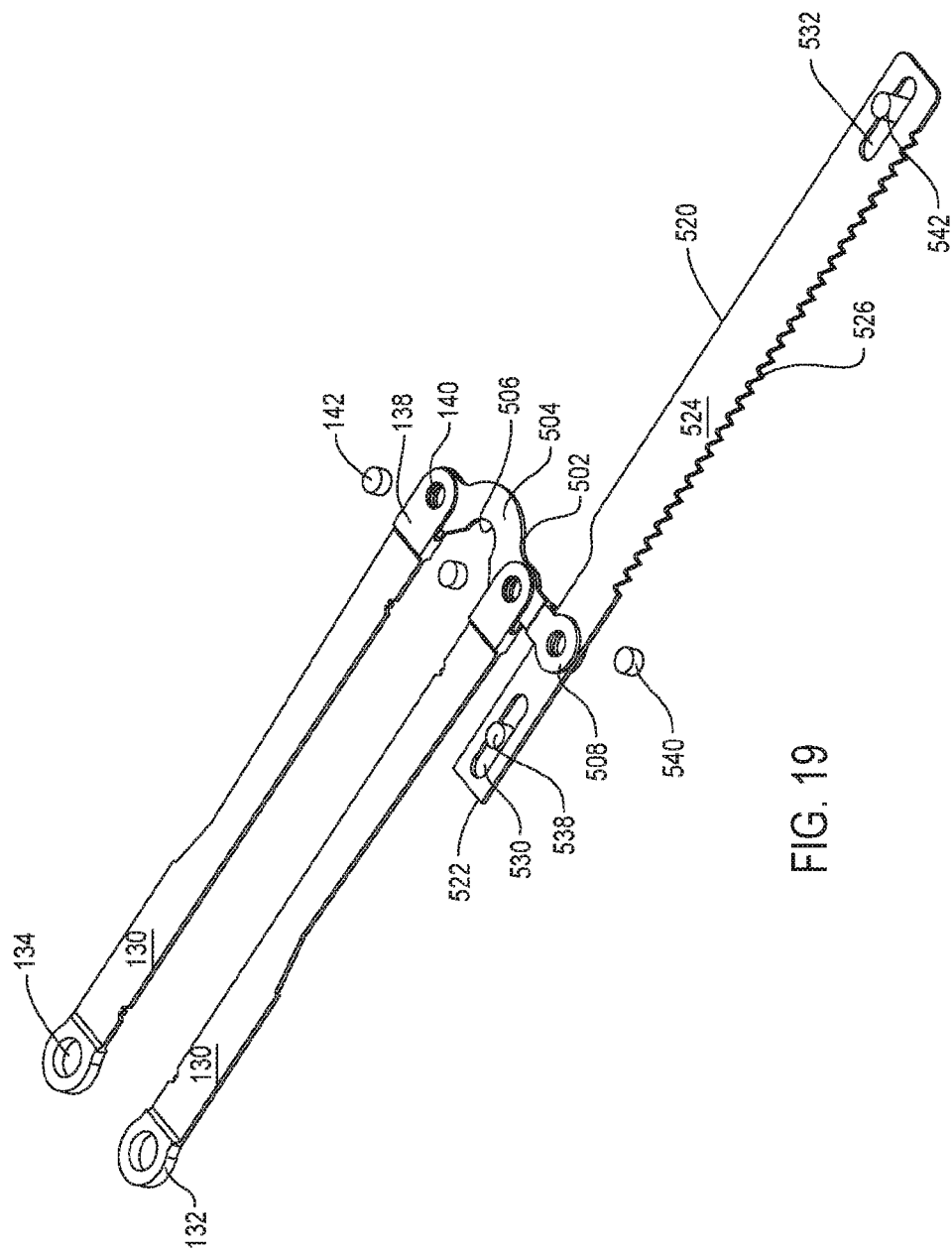
FIG. 19 is a perspective view of the drive link-and-blade sub-assembly of the cartridge of FIG. 17.

The saw blade 520 is an elongated, planar structure, as seen best in FIG. 19. The saw blade includes a base 522. Base 522 is dimensioned so seat in the space defined by the opposed spaced apart inner faces of the bottom and top plates 450 and 480, respectively, and on one side inner tine 110 and, on the opposed side, distal section 472 of outer tine 470. Forward of the base 522, the blade has a head 524, alternatively identified herein as a body 524. The blade is further formed so that teeth 526 extend forward from the elongated face of the body 524. More particularly, the teeth 526 extend forward from the face of the body directed to the side face 448 of the guide bar 442. Blade 520 is formed so that teeth have a width, the dimension along axes perpendicular to the longitudinal axis through the blade, that is sufficient so a kerf cut by the teeth is of sufficient width that at least the portion of beam 466 immediately adjacent blade 520 can be received in the kerf.

Saw blade 520 is formed to have two oval shaped openings 530 and 532 the major axes of which are parallel to the longitudinal axis of the blade. Opening 530 is located in base 522. Opening 532 is located in the end of blade body 524 spaced from the base 522. While not seen in the drawings, it should be understood that the blade is formed with a third oval opening. This opening is located in the base 522 so as to between opening 530 and the body of the blade. The major axis of this opening is perpendicular to the major axis of opening 530. The below described pin 540 extends through this opening.

When cartridge 440 is assembled, the base 522 of the blade seats in the void space internal to the guide bar 442 defined by the opposed bottom plate 450 and top plate 480 and tine 110 and distal section 472 of tine 470. The free end of blade body 524 seats in the space between the distal section of distal beam 466 and arm 468 and between plates 490. The components are dimensioned so that when the blade 520 is so seated the face of the blade body 524 opposite the face from which teeth extend is in close proximity too if not abutting the adjacent side face of distal beam 466. Also it should be understood that the blade 520 and more particularly, teeth 524 are configured so the kerf cut by the teeth will be of sufficient width to receive distal beam 466. It is further understood that the components of the cartridge 440 are selected so the kerf cut by blade 520 is less than the side-to-side thickness across the adjacent distal foot 488.

Two pins 538 and 542, hold the blade 520 to the guide bar so the blade is able to engage in reciprocal motion. Pin 538 extends through openings 454 and 483 in, respectively, the bottom plate 450 and top plate 480 and opening 530 in the blade. Pin 542 is seated in the holes 494 formed in the end plates and extend through opening 532 in the blade body 524. A pin 540 connects pivot link 502 to the blade 520. The opposed ends of pin 540 are seated in fingers 506. The pin extend through the oval opening in the blade base 522 adjacent the blade body 524.

Cartridge 440 is attached to the saw 30 using the same general steps used to attach the previously described cartridges of this invention to the saw.

Saw is positioned adjacent the bone to be cut. This bone is typically the sternum. The saw is properly positioned when the toe 489 integral with the distal foot 488 of the cartridge is located immediately adjacent the underside of the bone to be cut. Once cartridge 440 is properly positioned, the saw motor 42 is actuated to reciprocate the blade 520. More specifically the oscillation of the drive pins reciprocates the drive links 130. The reciprocating motion of the drive links 130 oscillates the pivot link 502 around the head 114 of the inner tine 110. The oscillation of the pivot link 502, is through pin 540 transferred to the blade 522. More specifically, the oscillations of the pivot link cause the blade to reciprocate back and forth along the longitudinal axis that extends through the blade. The blade teeth 526 therefore cut the bone against which the blade 520 is pressed.

As the cartridge cuts through the bone, the surgeon holds the saw so the distal foot 488 presses against the underside of the bone. As long as the surgeon holds the saw 32 and cartridge 440 in this position, the blade 520 will not bear against tissue below the bone. This prevents the unintended cutting of the tissue below the bone.

A difference between the cartridges 210 and 440 is that the distance between the cutting teeth 526 and the trailing end of beam 466 of cartridge 440 is less than the distance between teeth 304 and the trailing side 218 of cartridge 210. This makes it easier to turn cartridge 440 in a kerf than to turn cartridge 210 in kerf of the same width. Thus, cartridge 440 is especially useful for form a cut in the bone that is not linear in direction.

It should also be understood that cartridge 440 is typically designed as a use once item. This means that each time the cartridge is used, the practitioner is assured that the beam 466 that connects the distal foot 488 to the guide bar is straight and in line with the blade 520.

It should further be understood that while cartridge 440 includes a blade 520 that reciprocates, the cartridge can be attached to and actuated by a saw 30 designed to actuate a cartridge with a sagittal blade. This means that a medical facility using cartridge 440 of this invention does not have to provide a saw separate from the saw 30 used to actuate a blade that engages in sagittal motion in order to actuate a blade that engages in reciprocal motion.

FIG. 21 illustrates how an alternative saw blade 560 may be fitted to cartridge 440. Saw blade 560, as seen in FIG. 22, includes a base 562 similar to base 522 of blade 520. A difference between the two blades 520 and 560 is that base 562 is shorter than base 522. A blade body 564, similar to blade body 524, extends from base 562 of blade 560. Previously described teeth 526 extends outwardly from the exposed elongated face of blade body 564.

Blade 560 is further formed to have a circular opening 568 in the base 562. Opening 568 is the opening in the blade that receives the previously described pin 540. The blade 560 is further formed to have an elongated, oval shaped opening 570 in the end of the body 564 spaced from the base 562. The blade 560 is formed so that the major axis of the opening 570 is angled relative to the longitudinal axis through the blade 560. More particularly, extending from the end of opening 570 adjacent the free end of the blade body 564 towards the base 562, the major axis of opening 570 angles away from the face of the body 564 from which the teeth 526 extend.

When a version of cartridge 440 in which blade 560 is installed is assembled, the base 562 seats in the head 444 of the guide bar 442. The free end of body 564 seats in foot 488. Pin 540 extends through opening 568. Pin 542 is disposed in opening 570.

When a cartridge 440 with blade 560 is actuated, the drive links 130 and pivot link 502 move as previously described. The oscillation of pivot link 502 is, through pin 540 transferred to the blade 560. More particularly it should be understood that pin 540 engages in a movement along a loop. The movement of the pin 540 causes a like movement of the blade base 562. The movement of the free end of blade body 564 is constrained by portion of the body that defines the opening 570 in which pin 542 is seated. As a result of the blade body 564 being so constrained, the blade, when actuated, engages in reciprocal movement along a curved path. The motion of the blade thus has a longitudinal component in which the blade 560 reciprocates between the guide bar 442 and the foot 488. The motion of the blade also has a lateral component in which the blade moves towards and away from the distal beam 466. Thus while this movement is non-linear, since at least a component of the movement is longitudinal, for the purposes of this invention, the movement is considered a reciprocal loop motion.

V. Alternative Embodiments

The above is directed to specific versions of the invention. Other versions of the invention may have features different from what has been described. It should also be understood that the various versions of the invention may be combined. Likewise not all versions of each described cartridges may include all the features described as being associated with that cartridge.

For example, when the guide bar is provided with a structural member to reduce the weight of the saw and cartridge in the hand of the surgeon, the guide bar may only be provided with a single member, a single arm. It may not be necessary to provide this arm with fingers or like features that penetrate the tissue against which the arm is pressed. In the illustrated version of the invention, the arm includes a shoulder 80 and a forearm 82 that is angled from the shoulder. In some versions of the invention, the extension, the arm that extends from the guide bar may have an alternative shape. For example, the extension may be linear in shape. Further in the illustrated version of the invention, the arm extends slightly forward of the most proximal space in which the teeth of the blade sweep. In an alternative version of the invention, this arm may not extend forward of the location of the blade teeth. Alternatively, depending on the construction of the cartridge, there may be a reason to construct this at least one extension so the distal end of the extension is located forward of the most distally located teeth integral with the blade 150.

It should be understood from the description of cartridge 410 that there is no requirement that in all versions of the invention the structural member that limits movement of the bar always have a side-by-side width that is equal to or less than the width of the rest of the bar. Thus, some versions of the invention guide bar 62 and formed so that the forearms 82 and any teeth 84 are have a side to side thickness greater than the side to side thickness of the portion of the guide arm from which the adjacent blade 150 extends. More particularly the forearms and any teeth have a side-to-side thickness that is greater than the width of the kerf cut by the blade 150. This feature makes it possible to, after the cut is formed, rest the forearm and any teeth on a sections of the bone that have been cut. More particularly, the forearm or teeth rest on the sections of the bone on the opposed sides of the cut.

The structural component that serves as a stop that limits the upward movement of the cartridge may be different than the described recessed surface 222. For example in some versions of the invention, the cartridge may be provided with a tab that extends forward of the blade 292. This tab is formed to have a planar surface adjacent the teeth of the blade. This plane is contained in a plane that intersects the plane in which the blade is oriented. It should be understood that in this version of the invention the kerf cut by the blade will not be so wide as to fully receive this stop. The kerf will be of sufficient width to receive the portion of the guide bar located immediately proximal to the teeth.

Likewise in versions of the invention in which the structural member of the guide bar is a stop there is no requirement that in all versions of the invention the cartridge be designed so the blade reciprocates on a linear path. In some versions of the invention, the blade may be mounted to the cartridge so as to oscillate in an arc, in other words engage in sagittal motion. Similarly, in versions of the invention in which the structural member is a pivot arm, the blade may be mounted to the guide bar so as to be able to reciprocate linearly.

There is no requirement in all versions of the invention that the blade have a length greater than the width of the portion of the guide bar mounted to the associated saw. In some versions of the invention the exposed portion of the blade, the teeth, may subtend a line that is smaller in width than the proximal portion of the guide bar. This is especially true for versions of the invention designed to perform small bone surgery. Small bone surgery is generally surgery on the hand, the foot, the skull or the spine.

Similarly, there is no requirement that in all versions of the invention the blade be constructed so that the head and teeth have a width greater than that of the base. Blade 520 and 560, for example may be constructed so the heads and teeth of these blades have a width equal to their basis. The significant design requirement is that the kerf cut by the teeth of blades 520 and 560 be of sufficient depth to accommodate at least the portion of the beam 466 that immediately follows the blade into the bone. It should of course be recognized that in some versions of cartridge 440 it may be useful to provide a blade that is designed so as to have a head, or at least teeth, that have a thickness greater than the thickness of the base of the blade.

Likewise the invention is not limited to assemblies that include two drive links for pivoting the blade. Some cartridges of this invention may have a single drive link or three or more drive links. In versions of the invention with a single drive link the distal end of this link may be connected to a pivot link. The pivot link is connected to the blade to reciprocate the blade. More particularly it is anticipated that in these versions of the invention, one end of the pivot link may be pivotally mounted to the bar. For example, this end of the pivot link may be ring shaped. The link is pivotally attached to the bar by a pin that extends through the center of the ring. The opposed end of the pivot link is attached to the blade. In these versions of the invention the drive link is attached to a section of the pivot link located between the end of the link pivotally attached to the bar and the end of the link to which the blade is attached.

Further it is within the scope of this invention to provide a cartridge wherein the moving blade extends laterally away from a side surface of the guide bar. In these versions of the invention, the guide bar may be constructed so that a stop protrudes outwardly from the plane of the bar. Typically this stop is located slightly forward of the distal end terminus of the zone of travel of the teeth integral with blade.

It should be appreciated that in versions of the invention wherein a pivot link is employed to transfer motion to the blade head may also be employed in cartridges of this invention that do not include structural features that limit movement of the cartridge relative to the tissue against which the blade is pressed.

Thus some reciprocating cartridges of this invention may not have a structural feature that limit the movement of the bar.

Similarly some cartridges of this invention may include the pivot link and features for retaining the blade in the cartridge and not have a structural feature that limits the movement of the bar. Thus it may be desirable to provide this type of cartridge when it is desirable to provide a cartridge with moving components that are collectively designed to minimize vibration and for which it is not necessary to provide a feature that limits movement of the bar relative to the tissue against which the tissue is applied. This type of cartridge may include a blade that moves in a sagittal motion or a blade that engages in a reciprocal motion.

It should likewise be understood that in some versions of the invention wherein the bar is formed to retain the blade, the bar may only have a single internal void space for receiving a complementary portion of the blade.

Likewise the presence of one or more legs 412 spaced apart from the arcuate beam 414 of the blade may be present in a cartridge of this invention without requiring the blade to be connected to the one or more drive links 130 by a pivot link. This versions of the cartridge may be useful when it is desirable to for a given radius at the distal end of the blade reduce the mass of the blade without requiring the cartridge to be designed so that the point around which the blade pivots is proximal to the axis around which the blade is attached to the bar.

Similarly, alternative means may be provided to couple the pivot link to the blade so these two components are able to both pivot and move longitudinally relative to each other. At the simplest, this assembly may consist of forming the pivot link with a notch that extends proximally inwardly from a distally directed face of the link. The blade has a toe that is seated in this notch. Collectively the pivot link notch and blade toe are shaped to allow the pivot link and blade to both pivot and move longitudinally relative to each other.

Accordingly, it is an object of the appended claims to cover all such variations and modifications that come within the true spirit and scope of this invention.

What is claimed is:

1. A surgical saw blade cartridge, said cartridge comprising:
   a bar having at least one feature shaped to cooperate with a complementary component of a saw so the bar can be releasably secured to the saw, and the bar further including a first plate and an opposed second plate defining a space therebetween;
   a blade that includes a base that is moveably disposed at least in part in the space between the plates of the bar and a head integral with the base that is located outside of the bar, the head having teeth able to cut living tissue and the teeth having a width such that a kerf cut by the teeth of the head can receive a portion of the bar adjacent the blade head; and
   at least one drive link that extends through the bar that is moveable within the bar and that has a proximal end configured for attachment to a drive component of the saw and has a distal end connected to the base of the blade wherein a reciprocation of the at least one drive link by the saw component results in an oscillation of the blade, further wherein the bar is further formed to have at least one structural member located adjacent the blade head that extends forward of the blade head so that when the head cuts into tissue the structural member bears against uncut tissue adjacent the kerf formed by the blade head so as to limit a movement of the bar.

2. The surgical saw blade cartridge of claim 1, wherein the bar is further formed and said blade is mounted to said bar so that at least a portion of said blade head is able to oscillate in the space between a portion of the plates located proximal to said blade head.

3. The surgical saw blade cartridge of claim 1, wherein:
   the blade head has opposed ends;
   the bar has two said structural members and each said structural member extends forward of the blade head adjacent a separate end of the blade head.

4. The surgical saw blade cartridge of claim 1, wherein, said at least one structural member is shaped to present a curved profile to the tissue against which said at least one structural member is pressed so that the bar can be pivoted around the tissue against which the at least one structural member bears.

5. The surgical saw blade cartridge of claim 1, wherein the at least one structural member comprises an arm from which a plurality of fingers extend, said fingers being sections of said structural member that bear against the tissue.

6. The surgical saw blade cartridge of claim 1, wherein the bar lies in a plane; and the blade is mounted to the bar to oscillate back and forth around an axis that extends through the plane of the bar.

7. The surgical saw blade cartridge of claim 1, wherein the bar lies in a plane; the blade is mounted to the bar to oscillate back and forth along a path of travel that is in the plane of the bar; a proximal to distal longitudinal axis extends through the plane of the bar; and the blade is mounted to the bar to oscillate along a path of travel that is parallel or in registration with the longitudinal axis through the bar.

8. The surgical saw blade cartridge of claim 7, wherein:
internal to the bar is a pivot link that is pivotally moveable in the bar;
the at least one drive link is connected to said pivot link to pivot said pivot link; and
said pivot link and the blade base are connected together so that a pivoting movement of said pivot link results in the oscillation of the blade.

9. The surgical saw blade cartridge of claim 1, wherein two drive links extend through the bar, and are connected to the base of the blade so as to oscillate the blade.

10. The surgical saw blade cartridge of claim 1, wherein:
the bar has a proximal section and a beam that extends forward from the proximal section;
the blade is mounted to the bar to extend forward from the proximal section and be located adjacent to the beam, the beam having a thickness; and
the at least one structural member comprises a foot attached to an end of said beam that is spaced from the bar proximal section said foot having a thickness greater than the thickness of said beam.

11. The surgical saw blade cartridge of claim 1, wherein said at least one structural member is positioned relative to the rest of the bar and the blade to limit an extent the bar can be pushed into the tissue towards which the cartridge is directed.

12. The surgical saw blade cartridge of claim 1, wherein said at least one structural member is positioned relative to the rest of the bar and the blade to limit an extent the bar can be withdrawn away from the tissue towards which the cartridge is directed.

13. A surgical saw blade cartridge, said cartridge comprising:
a bar including a first plate and an opposed second plate defining a space therebetween and at least one of the plates having at least one feature shaped to cooperate with a complementary component of a saw so the bar can be releasably secured to the saw;
a blade that includes a base that is moveably disposed at least in part in the space between the plates of the bar and the blade having one of a body and a head integral with the base that is located outside of the bar, the one of the body and the head having teeth able to cut living tissue and having a width such that a kerf cut by the teeth of the head can receive a portion of the bar adjacent the blade head;
at least one drive link that extends through the bar that is moveable within the space between the plates of the bar and that has a proximal end configured for attachment to a drive component of the saw and a distal end that is connected to the blade so that a reciprocation of the at least one drive link by the saw component results in an oscillation of the blade; and
a pivot link disposed in said bar for pivoting movement within said bar and the distal end of the at least one drive link is pivotally connected to said pivot link to pivot said pivot link and the pivot link is rotatably connected to the blade, wherein; the blade is mounted to the bar and the blade base is connected to said pivot link so that the pivoting of said pivot link causes the oscillation of the blade.

14. The surgical saw blade cartridge of claim 13, wherein:
the bar is a planar structure; and
the at least one drive link, said pivot link and the blade are arranged so that the blade engages in the oscillation along a path of travel a component of which is parallel to a plane of the bar.

15. The surgical saw blade cartridge of claim 13, wherein:
the bar has a longitudinal axis that extends between opposed proximal and distal ends of the bar; and
the at least one drive link, said pivot link and the blade are arranged so that the blade engages in the oscillation, a component of which is in registration with or parallel to the longitudinal axis of the bar.

16. The surgical saw blade cartridge of claim 13, wherein the bar is further formed to have at least one structural member located adjacent the blade head that extends forward of the blade head and that has a thickness greater than a thickness of the teeth so that when the head cuts into tissue the at least one structural member bears against uncut tissue adjacent the kerf formed by the blade head so as to limit a movement of the bar.

17. The surgical saw blade cartridge of claim 13, wherein, plural drive links are disposed in the bar and the plural drive links are connected to said pivot link to pivot said pivot link.

18. The surgical saw blade cartridge of claim 13, wherein the bar and the blade are collectively configured so that when the blade engages in the oscillation, the blade undergoes a motion that has both a longitudinal component and a lateral component.

19. A surgical saw blade cartridge, said cartridge comprising;
a bar having at least one feature shaped to cooperate with a complementary component of a saw so the bar can be releasably secured to the saw and;
a blade that includes a base that is moveably disposed in the bar and a head integral with the base, the head having teeth located outside of the bar, the teeth able to cut living tissue and having a width such that a kerf cut by the teeth of the head can receive a portion of the bar adjacent the blade head; and
at least one drive link that extends through the bar that is moveable within the bar and that has a proximal end configured for attachment to a drive component of the saw and a distal end that is connected to the blade so that a reciprocation of the at least one drive link by the saw component results in an oscillation of the blade, wherein:
the bar is formed with at least one void that is internal to the bar;
the blade is formed with at least one structural feature that is seated in the at least one void wherein the bar and the blade are formed so that the at least one structural feature can move within the at least one void; and
a pivot link is disposed in said bar for a pivoting movement within said bar and the distal end of the at least one drive link is connected to said pivot link to pivot said pivot link; and
said pivot link and the blade are connected together so that the pivoting movement of said pivot link results in the oscillation of the blade and so that when said pivot link pivots said pivot link and the blade are able to engage in both a rotational movement and a longitudinal movement relative to each other.

20. The surgical saw blade cartridge of claim 19, wherein:
the bar, the at least one drive link, said pivot link and the blade are collectively configured and the blade is mounted to the bar so that the reciprocation of the at least one drive link results in the oscillation of the blade around an axis that extends through a plane of the bar.

* * * * *